(12) United States Patent
Gustafson et al.

(10) Patent No.: US 10,246,463 B2
(45) Date of Patent: Apr. 2, 2019

(54) HYPOXIA-INDUCIBLE FACTOR 1 (HIF-1) INHIBITORS

(71) Applicant: The United States of America, as represented by the Secretary, Department of Health and Human Services, Washington, DC (US)

(72) Inventors: Kirk R. Gustafson, Frederick, MD (US); Martin J. Schnermann, Rockville, MD (US); Susanna T. S. Chan, Frederick, MD (US); Paresma R. Patel, Rockville, MD (US); William D. Figg, Fairfax, VA (US); James B. McMahon, Frederick, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/563,851

(22) PCT Filed: Apr. 6, 2016

(86) PCT No.: PCT/US2016/026145
§ 371 (c)(1),
(2) Date: Oct. 2, 2017

(87) PCT Pub. No.: WO2016/164412
PCT Pub. Date: Oct. 13, 2016

(65) Prior Publication Data
US 2018/0093995 A1  Apr. 5, 2018

Related U.S. Application Data

(60) Provisional application No. 62/144,182, filed on Apr. 7, 2015.

(51) Int. Cl.
*A61K 31/519* (2006.01)
*C07D 487/16* (2006.01)
*A61K 45/06* (2006.01)

(52) U.S. Cl.
CPC .......... *C07D 487/16* (2013.01); *A61K 31/519* (2013.01); *A61K 45/06* (2013.01)

(58) Field of Classification Search
None
See application file for complete search history.

(56) References Cited

FOREIGN PATENT DOCUMENTS

WO  WO 2010/006189 A2  1/2010

OTHER PUBLICATIONS

CAS No. 2700085-84-2, *ChemicalBook* 2010, 1 pg.
CAS No. 268546-04-9, cas.ChemNet.com, downloaded Apr. 25, 2015, 1 pg.
CAS No. 268546-69-6, cas.ChemNet.com, downloaded Apr. 25, 2015, 1 pg.
CAS No. 268547-00-8, *Guidechem* 2010-2015, 1 pg.
CAS No. 331456-13-4, *Look Chemical—The Online Chemical Buyer's Guide*, LookChemical Ltd. 2010, 1 pg.
Chan, et al. "Structural Elucidation and Synthesis of Eudistidine A: An Unusual Polycyclic Marine Alkaloid that Blocks Interaction of the Protein Binding Domains of p300 and HIF-1[alpha]" *Journal of the American Chemical Society* 137, No. 16 (2015): 5569-5575.
International Search and Written Opinion for PCT/US2016/026145, dated May 18, 2016, 12 pages.
Semenza, "HIF-1 mediates metabolic responses to intratumoral hypoxia and oncogenic mutations," *The Journal of Clinical Investigation* Sep. 2013, 123(9):3664-3671.

*Primary Examiner* — Deepak R Rao
*Assistant Examiner* — Laura M Daniel
(74) *Attorney, Agent, or Firm* — Klarquist Sparkman, LLP

(57) ABSTRACT

Embodiments of small molecule inhibitors of hypoxia inducible factor 1 (HIF-1) and pharmaceutical compositions thereof are disclosed. The disclosed compounds suppress HIF-1 activity by inhibiting the interaction between the HIF-1 α subunit and transcriptional co-activator protein p300. Embodiments of methods for making and using the small molecule inhibitors are also disclosed.

22 Claims, 9 Drawing Sheets

Scheme 1

Scheme 2

HYPOXIA-INDUCIBLE FACTOR 1 (HIF-1) INHIBITORS

CROSS-REFERENCE TO RELATED APPLICATION

This is the U.S. National Stage of International Application No. PCT/US2016/026145, filed Apr. 6, 2016, which was published in English under PCT Article 21(2), which in turn claims the benefit of the earlier filing date of U.S. Provisional Application No. 62/144,182, filed Apr. 7, 2015, which is incorporated by reference in its entirety herein.

FIELD

This disclosure concerns embodiments of small molecule inhibitors of hypoxia-inducible factor 1 (HIF-1), as well as methods of making and using the small molecule inhibitors.

BACKGROUND

Low oxygen environments are a hallmark of solid tumors and the transcription of many hypoxia-responsive genes needed for survival under these conditions is regulated by the heterodimeric transcription factor HIF-1 (hypoxia-inducible factor 1). The transcription factor HIF-1 is critical for initiating adaptive responses to low oxygen environments and maintaining cellular homeostasis. HIF-1 regulates the transcription of numerous hypoxia-responsive genes, including ones that modulate glycolysis and glucose flux, and those associated with vasodilation and angiogenesis such as vascular endothelial growth factor. Overexpression or dysregulation of HIF-1 function has been implicated in tumor progression, metastasis, resistance to chemotherapies, and poor clinical outcomes for a variety of tumor types.

Inhibition of HIF-1 activity has potential therapeutic applications for a variety of tumor types. HIF-1 is a heterodimer of α- and β-subunits, and the transcriptional activity of this complex is regulated by either the accumulation or turnover of the HIF-1α monomer. Under normoxic conditions HIF-1α is rapidly recycled in a process that involves hydroxylation of specific proline residues, followed by ubiquitination and proteasomal degradation of the monomer. When oxygen tension is low, HIF-1α accumulates in the nucleus where it dimerizes with the constitutively present HIF-1β subunit. This allows recruitment and binding of the transcriptional coactivator p300, a multidomain protein that not only plays a crucial role in HIF-1 activation but also has intrinsic histone acetyl transferase and polyubiquitin ligase activities.

Activation of HIF-1 requires binding of its α-subunit (HIF-1α) to the transcriptional co-activator protein p300. Inhibition of the p300/HIF-1α interaction is an attractive approach to suppress HIF-1 activity. The essential binding interaction between p300 and HIF-1 that facilitates hypoxia-induced transcription involves the cysteine histidine-rich domain 1 (CH1) of p300 and the C-terminal transactivation domain (C-TAD) of HIF-1α.

Small molecule inhibitors of specific protein-protein interactions are quite rare, due in part to the large surface contact areas that are involved. Many of the small molecules that can inhibit protein-protein interactions have poor specificity or low potencies, with inhibitory concentrations often observed in the millimolar range. Block et al. designed and synthesized a series of dimeric epidithiodiketopiperazines, and the lead compound was shown to selectively inhibit the p300/HIF-1α interaction (*J. Am. Chem. Soc.* 2009, 131: 18078-18088). In cellular assays it downregulated the expression of hypoxia-responsive genes, and in a murine model it significantly reduced in vivo tumor growth (Dubey et al., *J. Am. Chem. Soc.* 2013, 135:4537-4549). This study served as a proof of principle that validated small molecule targeting of the p300/HIF-1 interaction to inhibit tumors. The actinobacterial metabolite novobiocin, an aminocoumarin glycoside, was shown to disrupt the p300/HIF-1α interaction by directly binding to the HIF-1α C-TAD domain (Wu et al., *PLoS One* 2013, 8:362014).

HIF-1 also plays a role in other conditions besides tumors, such as malaria and inflammatory conditions. Inflamed and injured tissue may exhibit hypoxia in addition to other biomarkers of inflammation. Inflammatory mediators, such as proinflammatory cytokines, as well as certain bacterial and viral compounds, can activate HIF-1 to produce an inflammatory response.

Accordingly, HIF-1 inhibition is believed to inhibit tumor progression, metastasis, and resistance to chemotherapies, inhibit malarial infection, and/or ameliorate conditions including a hypoxia-mediated inflammatory response.

SUMMARY

Small molecule inhibitors of the p300/HIF-1α interaction are disclosed, along with pharmaceutical compositions comprising the small molecule inhibitors, and methods of making and using the small molecule inhibitors. Embodiments of the disclosed small molecule inhibitors have a chemical structure according to Formula I or a pharmaceutically acceptable salt thereof.

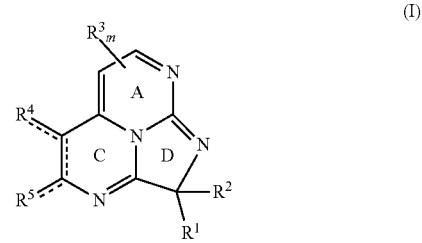

(I)

wherein each bond depicted as "=====" is a single or double bond as needed to satisfy valence requirements; $R^1$ is halo, aliphatic, heteroaliphatic, alicyclic, heteroalicyclic, aryl, heteroaryl, $-OR^a$, $-SR^a$, $-COOR^a$, or $-N(R^a)_2$, and $R^2$ is $-OR^a$, $-SR^a$, alicyclic, heteroalicyclic, aryl, or heteroaryl; or $R^1$ and $R^2$ together are $=O$ or $=S$; each $R^3$ independently is aliphatic, heteroaliphatic, aryl, heteroaryl, $-COOR^a$, or $-C(O)N(R^a)_2$; m is 0, 1, or 2; $R^4$ and $R^5$ independently are hydrogen, aliphatic, heteroaliphatic, halo, $-OR^a$, $-SR^a$, oxygen, or sulfur, or $R^4$ and $R^5$ together with the carbon atoms to which they are bound define ring B where ring B is aryl, heteroaryl, alicyclic, or heteroalicyclic; and each $R^a$ independently is hydrogen or alkyl. In some embodiments, m is 0. Exemplary pharmaceutically acceptable salts include hydrochloric acid salts, acetic acid salts, or trifluoroacetic acid salts.

In some embodiments, the compound has a chemical structure according to Formula II:

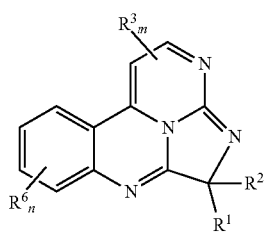

(II)

wherein n is 0, 1, 2, 3, or 4; and each $R^6$ independently is aliphatic, heteroaliphatic, alicyclic, heteroalicyclic, aryl, heteroaryl, halo, —$OR^a$, —$SR^a$, —$COOR^a$, or —C(O)N($R^a$)$_2$, where each $R^a$ independently is hydrogen or alkyl. In some embodiments, m is 0, n is 0, or m and n are 0.

In any or all of the above embodiments, $R^1$ may be hydroxyl, lower alkoxy, lower aliphatic, alicyclic, or aryl. In some embodiments, $R^1$ is hydroxyl, lower alkoxy, optionally substituted lower aliphatic, optionally substituted phenyl, optionally substituted imidazolyl, optionally substituted indolyl, optionally substituted pyrrolyl, optionally substituted pyrazolyl, optionally substituted pyridyl, optionally substituted furyl, optionally substituted naphthyl, or optionally substituted cyclohexyl.

In any or all of the above embodiments, $R^2$ may be aryl or heteroaryl. In some embodiments, $R^2$ is optionally substituted phenyl, such as ortho or para substituted phenyl, optionally substituted naphthyl, or optionally substituted pyridyl In any or all of the above embodiments, $R^1$ may be:

—$OR^a$, —$SR^a$,

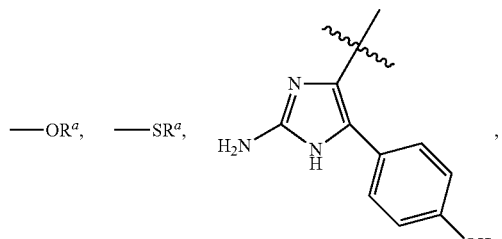

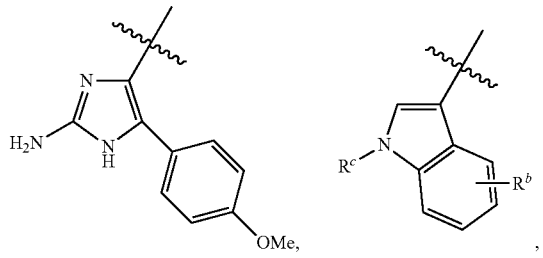

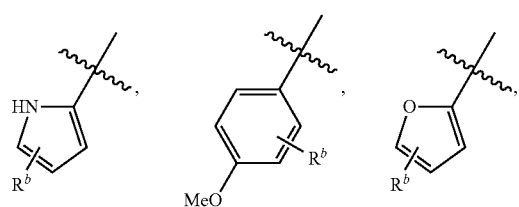

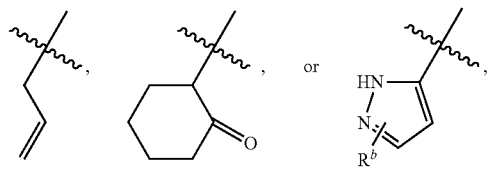

wherein $R^b$ is hydrogen, halo, aliphatic, heteroaliphatic, —$OR^a$, —$SR^a$, —C(O)$OR^a$, or —C(O)N($R^a$)$_2$; and $R^c$ is hydrogen, aliphatic, or heteroaliphatic.

In any or all of the above embodiments, $R^2$ may be:

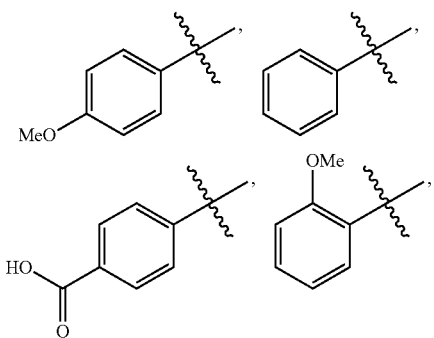

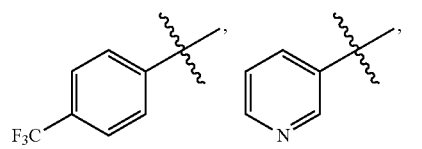

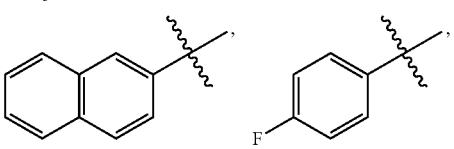

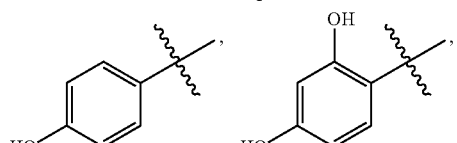

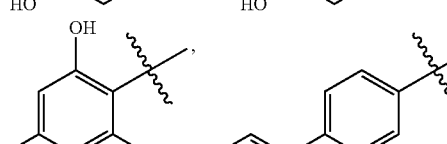

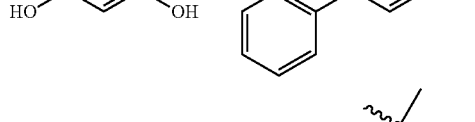

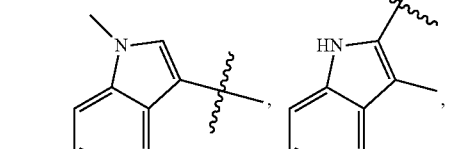

-continued
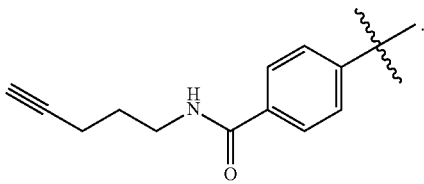
Exemplary compounds according to Formula I include:
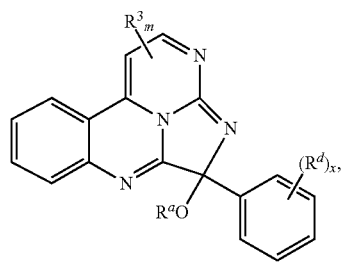
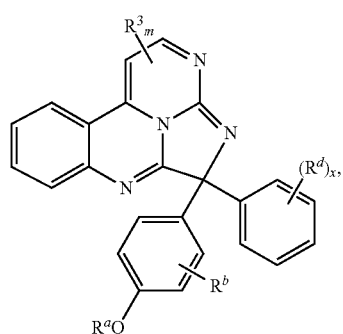
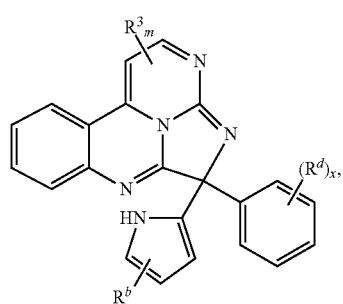
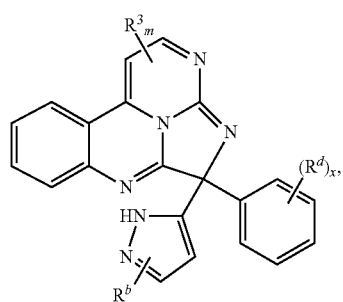
-continued
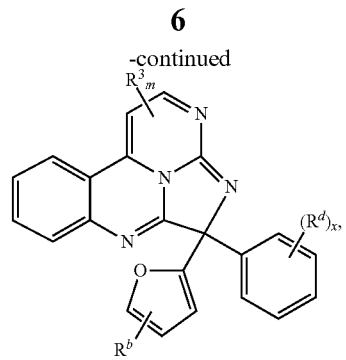
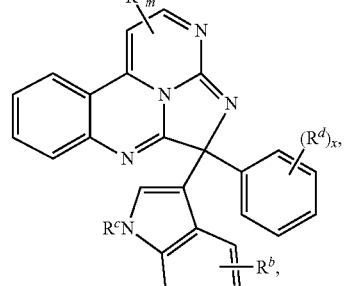
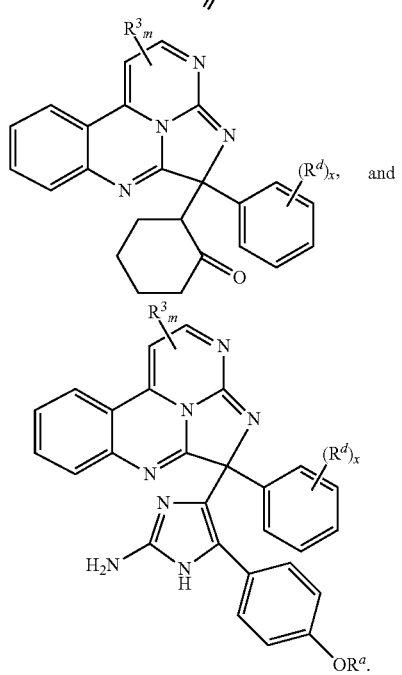
wherein $R^b$ is hydrogen, halo, aliphatic, heteroaliphatic, —$OR^a$, —$SR^a$, —C(O)$OR^a$, or —C(O)N($R^a$)$_2$; $R^c$ is hydrogen, aliphatic, or heteroaliphatic; each $R^d$ independently is hydroxyl, halo, aliphatic, heteroaliphatic, amido, —$OR^a$, —$SR^a$, or aryl; and x is 0, 1, 2, or 3. In some embodiments, m is 0. In any or all of the above embodiments, embodiments, x may be 0 or 1. In any or all of the above embodiments, $R^a$ may be H or methyl.
Exemplary species include:
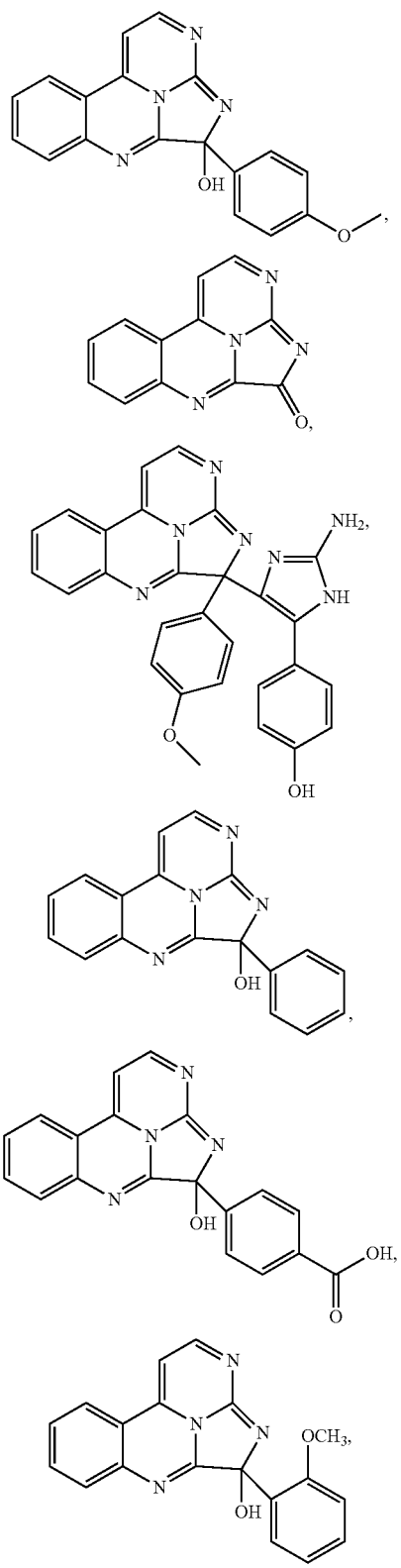
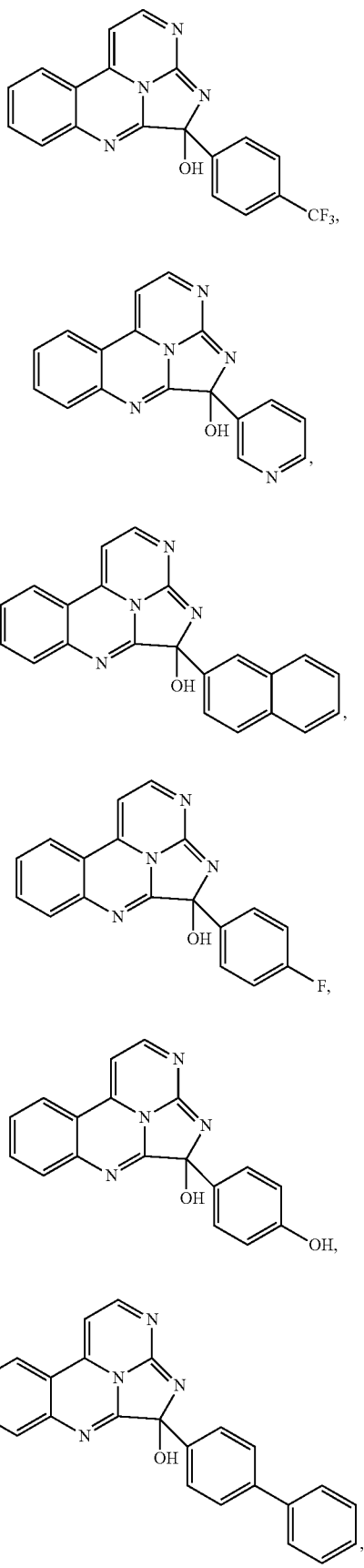

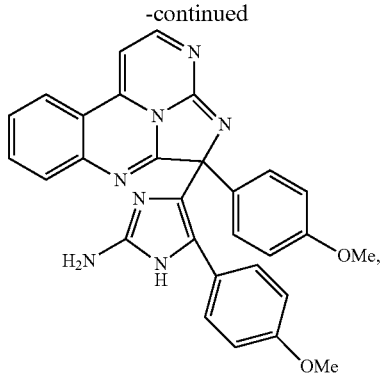
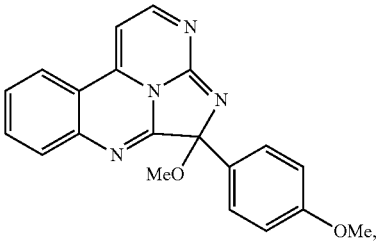
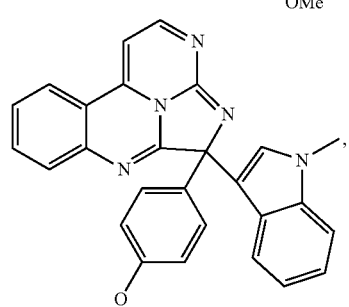
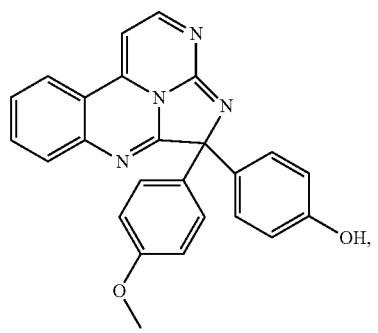
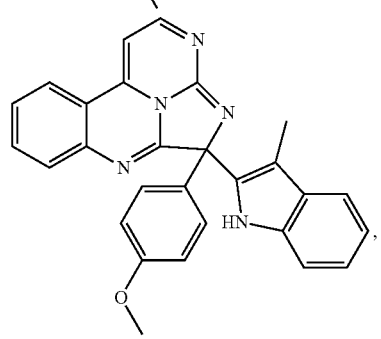
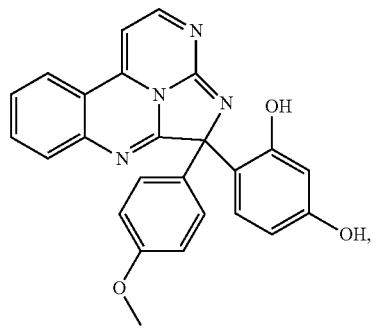
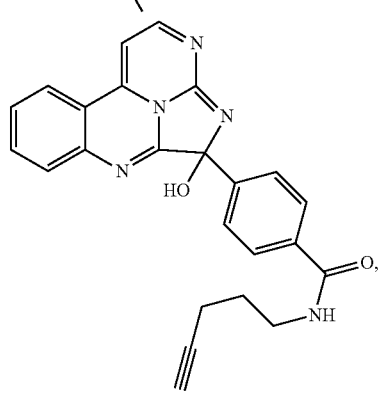
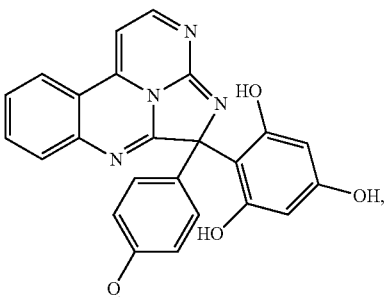
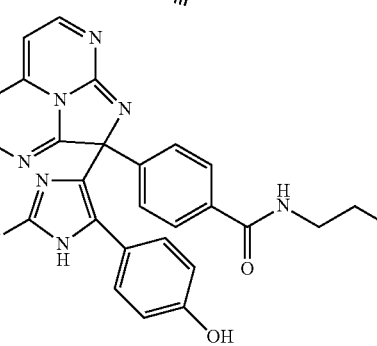
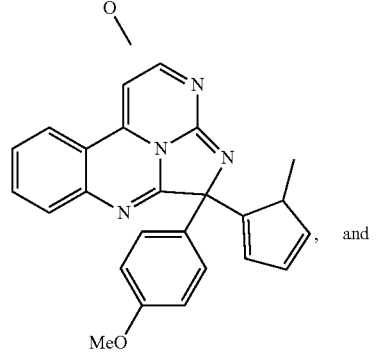

-continued

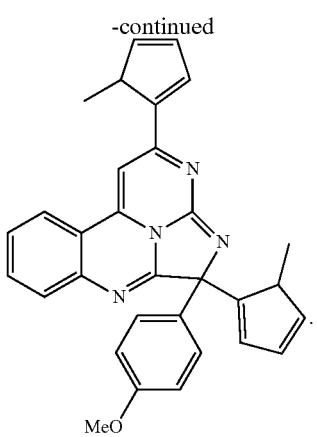

A pharmaceutical composition includes at least one compound as disclosed herein or a pharmaceutically acceptable salt thereof, and at least one pharmaceutically acceptable carrier. The pharmaceutical composition may include a second therapeutic agent, such as an anticancer agent, an antimalarial agent, or an anti-inflammatory agent.

A method for making a compound according to Formula I includes (i) heating compound A, wherein R' is hydrogen or $R^3$, with 1,1-dimethoxy-N,N'-dimethylmethanamine to form an intermediate

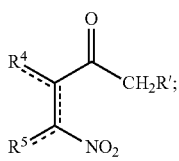

(A)

(ii) refluxing a solution comprising the intermediate and guanidine hydrochloride to form compound B

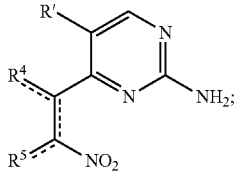

(B)

(iii) hydrogenating compound B with a catalyst comprising Pd/C to form compound C

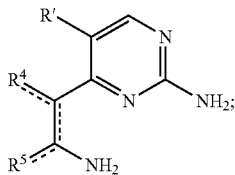

(C)

(iv) oxidizing $R^2$—C(O)CH$_2$X to form $R^2$—C(O)C(O)H, where X is halo; (v) if $R^2$ is —OH or —SH, heating compound C with the $R^2$—C(O)C(O)H for an effective period of time to form compound D where A is O or S; or if $R^2$ is other than —OH or —SH, heating compound C with the $R^2$—C(O)C(O)H for an effective period of time, followed by addition of an oxidant to form compound E

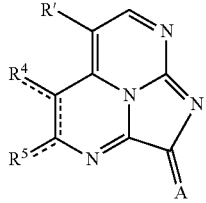

(D)

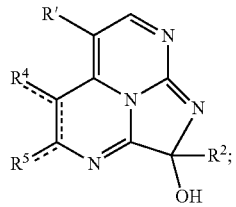

(E)

and
(vi) optionally reacting compound E with a nucleophile comprising $R^1$ ($R^1$H in some examples) to form compound F (F)

A method for inhibiting hypoxia-inducible factor 1 (HIF-1) activity includes contacting a cell with an effective amount of a compound as disclosed herein or a pharmaceutically acceptable salt thereof. In some embodiments, the method further includes contacting the cell with a second therapeutic agent. Exemplary second therapeutic agents include anticancer agents, antimalarial agents, and anti-inflammatory agents.

In any or all of the above embodiments, contacting the cell may include administering to a subject a therapeutically effective amount of (i) the compound or pharmaceutically acceptable salt thereof, or (ii) a pharmaceutical composition comprising the compound or pharmaceutically acceptable salt thereof and at least one pharmaceutically acceptable carrier. In some embodiments, the subject has been identified as being in need of treatment for a solid tumor, malaria, or an inflammatory condition mediated by HIF-1. In any or all of the above embodiments, the subject may be administered a pharmaceutical composition comprising (i) the compound or pharmaceutically acceptable salt thereof, (ii) a second therapeutic agent, and (iii) at least one pharmaceutically acceptable carrier. In some embodiments, the subject is separately administered in any order (i) the compound or pharmaceutically acceptable salt thereof and (ii) a second therapeutic agent.

An embodiment of a compound as disclosed herein, or a pharmaceutically acceptable salt thereof, may be used as a medicament. In some embodiments, the medicament is formulated for treatment of a solid tumor, malaria, or an inflammatory condition mediated by HIF-1 (e.g., a malignant tumor, intestinal inflammation, lung inflammation, ischemia, atherosclerosis, myocardial infarction, rheumatoid arthritis, or a healing wound). The use may comprise administering a therapeutically effective amount of (i) the compound or pharmaceutically acceptable salt thereof, or (ii) a pharmaceutical composition comprising the compound or pharmaceutically acceptable salt thereof and at least one pharmaceutically acceptable carrier to a subject for treatment of a solid tumor, malaria, or an inflammatory condition mediated by HIF-1.

In one embodiment, a method for treating a solid tumor includes administering to a subject having a solid tumor a therapeutically effective amount of (i) a compound as disclosed herein or a pharmaceutically acceptable salt thereof or (ii) a pharmaceutical composition comprising the compound or pharmaceutically acceptable salt thereof and at least one pharmaceutically acceptable carrier. In an independent embodiment, a method for treating malaria includes administering to a subject having malaria or at risk of developing malaria a therapeutically effective amount of (i) a compound as disclosed herein or a pharmaceutically acceptable salt thereof or (ii) a pharmaceutical composition comprising the compound or pharmaceutically acceptable salt thereof and at least one pharmaceutically acceptable carrier. In another independent embodiment, a method for treating an inflammatory condition includes administering to a subject having an inflammatory condition mediated by hypoxia a therapeutically effective amount of (i) a compound as disclosed herein or a pharmaceutically acceptable salt thereof or (ii) a pharmaceutical composition comprising the compound or pharmaceutically acceptable salt thereof and at least one pharmaceutically acceptable carrier. The inflammatory condition may be a malignant tumor, intestinal inflammation, lung inflammation, ischemia, atherosclerosis, myocardial infarction, rheumatoid arthritis, or a healing wound.

The foregoing and other objects, features, and advantages of the invention will become more apparent from the following detailed description, which proceeds with reference to the accompanying figures.

DETAILED DESCRIPTION

Figure 1:
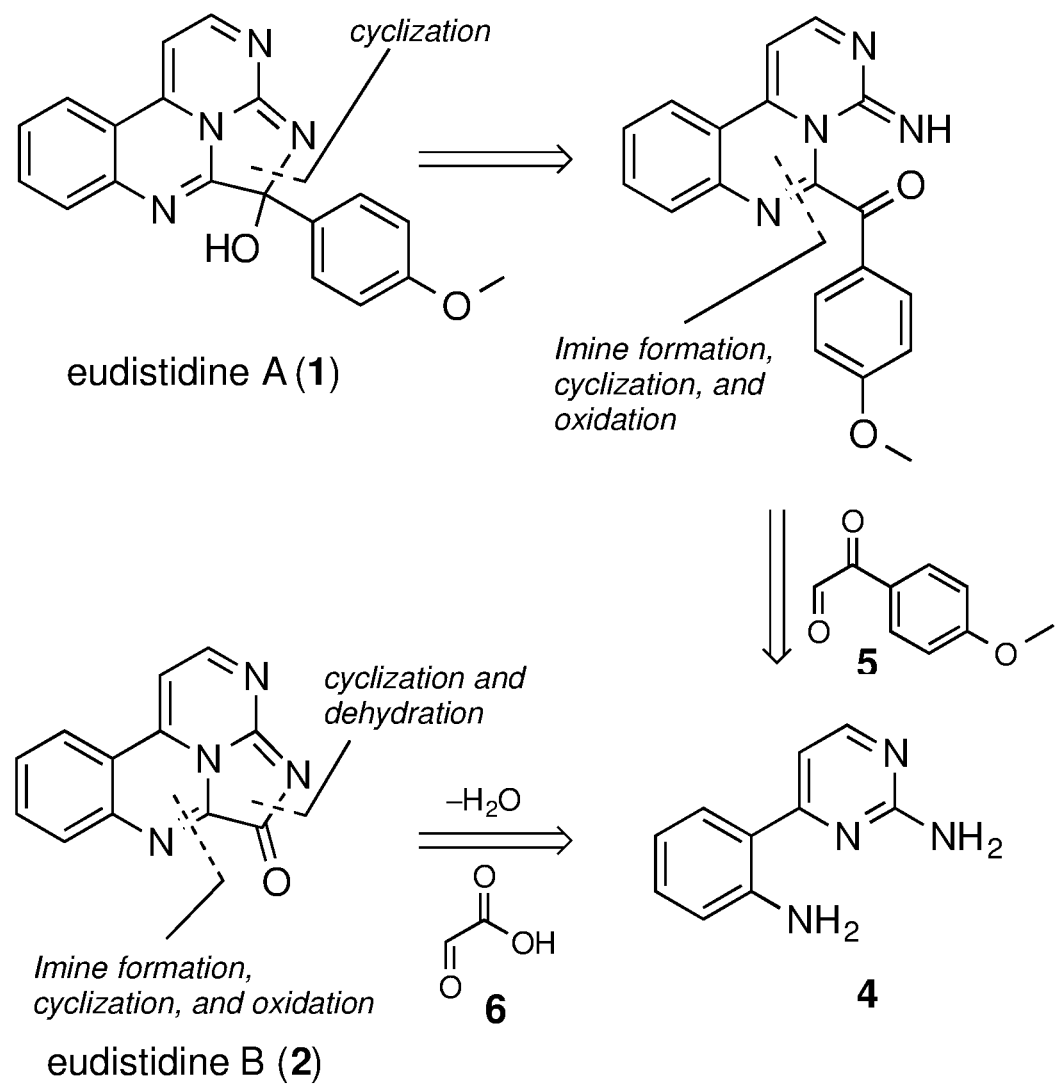
FIG. 1 is a scheme showing retrosynthetic analysis of eudistidines A (1) and B (2).

This disclosure concerns small molecule inhibitors of the p300/HIF-1α interaction, pharmaceutical compositions comprising the small molecule inhibitors, and methods of using the small molecule inhibitors. Embodiments of a method for making the small molecule inhibitors also are disclosed.

I. TERMS AND DEFINITIONS

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

In order to facilitate review of the various embodiments of the disclosure, the following explanations of specific terms are provided:

Administering: Administration by any route, for example oral, topical, intravenous, intraperitoneal, intramuscular, intralesional, intranasal, or subcutaneous administration, release from a suppository, or the implantation of a slow-release device (e.g., a mini-osmotic pump) to the subject. "Parenteral" administration is by any route other than through the alimentary tract and includes intravascular administration directly into a blood vessel, for example by intravenous or intra-arterial administration.

Alicyclic: A cyclic aliphatic compound, or radical thereof, that may be saturated or unsaturated, but is not aromatic. Alicyclic compounds or groups may be substituted or unsubstituted. Alicyclic compounds include cycloalkanes, cycloalkenes, bicyclic alkanes, polycyclic alkanes, and bicyclic alkenes. Unless expressly stated otherwise, an alicyclic compound or radical contains from three to twenty-five carbon atoms, more typically from four to twelve carbon atoms in the ring. Exemplary monocyclic alicyclic compounds include, but at not limited to, cyclopropane, cyclobutane, cyclopentane, cyclohexane, cycloheptane, cyclooctane, cyclopropene, cyclobutene, cyclopentene, cycloheptene, cyclooctene, and so on. Exemplary bicyclic alicyclic compounds include, but are not limited to, bicycloundecane, decalin, and norbornene.

Alkoxy: A radical (or substituent) having the structure —OR, where R is a substituted or unsubstituted alkyl. Methoxy (—OCH$_3$) is an exemplary alkoxy group. In a substituted alkoxy, R is alkyl substituted with a non-interfering substituent.

Alkyl: A hydrocarbon group having a saturated carbon chain. The chain may be cyclic, branched or unbranched. The term lower alkyl means the chain includes 1-10 carbon atoms. Unless otherwise specified, an alkyl group may be substituted or unsubstituted.

Aliphatic: A substantially hydrocarbon-based compound, or a radical thereof (e.g., $C_6H_{13}$, for a hexane radical), including alkanes, alkenes, alkynes, including cyclic versions thereof, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms. The term "lower aliphatic" refers to an aliphatic group containing from one to ten carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene carbon in an aliphatic chain, or up to one substituent for each carbon of a —C=C— double bond in an aliphatic chain, or up to one substituent for a carbon of a terminal methine group). Exemplary aliphatic substituents include, for instance, amino, amide, sulfonamide, halo, cyano, carboxy, hydroxyl, mercapto, trifluoromethyl, alkyl, alkoxy, alkylthio, thioalkoxy, arylalkyl, heteroaryl, alkylamino, dialkylamino, or other functionality.

Amido: A chemical functional group —C(O)N(R)(R') where R and R' are independently hydrogen, aliphatic, heteroaliphatic, haloaliphatic, aryl (such as optionally substituted phenyl or benzyl), heteroaryl, alkylsulfano, or other functionality.

Aryl: A monovalent aromatic carbocyclic group of, unless specified otherwise, from 6 to 15 carbon atoms having a single ring (e.g., phenyl) or multiple condensed rings which condensed rings may or may not be aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic. Unless otherwise specified, an aryl group may be substituted or unsubstituted.

Condensation: A type of chemical reaction in which two or more molecules combine with the separation of water, alcohol, or other simple substance.

Effective amount or therapeutically effective amount: An amount sufficient to provide a beneficial, or therapeutic, effect to a subject or a given percentage of subjects.

Heteroaliphatic: An aliphatic compound or group having at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, cyclic or acyclic, and include "heterocycle", "heterocyclyl", "heteroalicyclic", or "heterocyclic" groups.

Heteroaryl: A monovalent monocyclic or bicyclic aromatic radical of 5 to 10 ring atoms with each ring containing one, two, or three ring heteroatoms selected from N, O, or S, the remaining ring atoms being C. The aromatic radical is optionally fused to a phenyl or an optionally substituted heteroaryl ring or it is optionally substituted independently with one or more substituents, such as one or two substituents selected from alkyl, haloalkyl, heteroalkyl, aliphatic, heteroaliphatic, alkoxy, halo, cyano, nitro, aryl, optionally substituted heteroaryl, amino, monosubstituted amino, disubstituted amino, hydroxyamino, —OR (where R is hydrogen, haloalkyl, or optionally substituted phenyl), —S(O)$_n$—R (where n is an integer from 0 to 2 and R is alkyl, haloalkyl, optionally substituted phenyl, amino, mono or disubstituted amino), —C(O)R (where R is hydrogen, alkyl, haloalkyl or optionally substituted phenyl), —COOR (where R is hydrogen, alkyl or optionally substituted phenyl), —C(O)N(R')R" (where R' and R" are independently selected from hydrogen, alkyl, haloalkyl, or optionally substituted phenyl). In specific examples, the term heteroaryl includes, but is not limited to pyridyl, pyrrolyl, thiophene, pyrazolyl, thiazolyl, imidazolyl, pyrimidinyl, thiadiazolyl, indolyl, carbazolyl, azaindolyl, benzofuranyl, benzimidazolyl, benzthiazolyl, quinoxalinyl, benzotriazolyl, benzisoxazolyl, purinyl, quinolinyl, isoquinolinyl, benzopyranyl, and derivatives thereof. Unless otherwise specified, heteroaryl group may be substituted or unsubstituted.

Nucleophile: An ion or molecule that donates an electron pair to an atomic nucleus to form a covalent bond, a Lewis base. Nonlimiting examples of nucleophiles include hydroxide anions, alcohols, alkoxide anions, carboxylate anions, thiols, thiolate anions, thiolcarboxylate anions (RC(O)—S$^-$), dithiocarbonates (RO—C(S)—S$^-$), dithiocarbamates (R$_2$N—C(S)—S$^-$), azides, amines, nitrites, enols, organolithium reagents, and alkyl metal halides.

Oxidant or oxidizing agent: An element or compound in an oxidation-reduction reaction that accepts an electron from another species.

Pharmaceutically acceptable: The term "pharmaceutically acceptable" refers to a substance that can be taken into a subject without significant adverse toxicological effects on the subject.

Pharmaceutically acceptable carrier: Conventional pharmaceutically acceptable carriers are useful for practicing the methods and forming the compositions disclosed herein. *Remington's Pharmaceutical Sciences*, by E. W. Martin, Mack Publishing Co., Easton, Pa., 15th Edition, 1975, describes examples of compositions and formulations suitable for pharmaceutical delivery of the compounds herein disclosed. In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In some examples, the pharmaceutically acceptable carrier is a non-naturally occurring or synthetic carrier. The carrier also can be formulated in a unit-dosage form that carries a preselected therapeutic dosage of the active agent, for example in a pill, vial, bottle, or syringe.

Pharmaceutically acceptable salt: A biologically compatible salt of a compound that can be used as a drug, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. In some examples disclosed herein, the pharmaceutically acceptable salt is an acid addition salt. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Subject: An animal or human subjected to a treatment, observation or experiment.

Substituent: An atom or group of atoms that replaces another atom in a molecule as the result of a reaction. The term "substituent" typically refers to an atom or group of atoms that replaces a hydrogen atom on a parent hydrocarbon chain or ring.

Substituted: A fundamental compound, such as an aryl, heteroaryl, or alkyl compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a hydrocarbon may have a substituent bonded thereto, such as one or more halogens, an aryl group, a cyclic group, a heteroaryl group or a heterocyclic group.

Therapeutic agent or active agent: An agent that provides a beneficial, or therapeutic, effect to a subject or a given percentage of subjects.

Treating or treatment: With respect to disease, either term includes (1) preventing the disease, e.g., causing the clinical symptoms of the disease not to develop in a human or non-human animal that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

Tumor: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

Tumors of the same tissue type may be divided into tumor of different sub-types (a classic example being bronchogenic carcinomas (lung tumors) which can be an adenocarcinoma, small cell, squamous cell, or large cell tumor). Breast cancers can be divided histologically into scirrhous, infiltrative, papillary, ductal, medullary and lobular.

Tumors include original (primary) tumors, recurrent tumors, and metastases (secondary) tumors. A tumor recurrence is the return of a tumor, at the same site as the original (primary) tumor, after the tumor has been removed surgically, by drug or other treatment, or has otherwise disappeared. A metastasis is the spread of a tumor from one part of the body to another. Tumors formed from cells that have spread are called secondary tumors and contain cells that are like those in the original (primary) tumor. There can be a recurrence of either a primary tumor or a metastasis.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma).

II. EUDISTIDINES

A high-throughput screen for inhibitors of the protein binding domains of p300 (CH1) and HIF-1α (C-TAD) identified an extract of the marine ascidian *Eudistoma* sp. as active. Novel heterocyclic alkaloids—termed eudistidines A (1), B (2), and C (3)—were isolated from the extract and their structures assigned by spectroscopic analyses. The eudistidines contain an unprecedented tetracyclic core comprised of two pyrimidine rings fused with an imidazole ring, which also contains embedded guanidine and amidine functionalities.

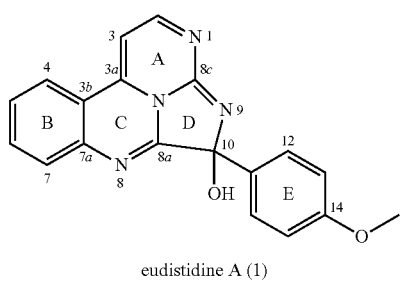

eudistidine A (1)

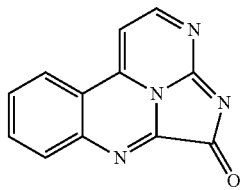

eudistidine B (2)

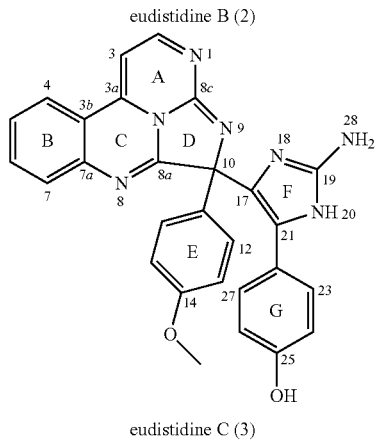

eudistidine C (3)

Embodiments of the disclosed naturally occurring eudistidines and analogs thereof have a chemical structure according to general Formula I or a pharmaceutically acceptable salt thereof:

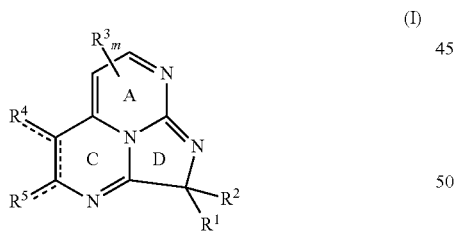

(I)

With respect to Formula I, each bond depicted as "-----" is a single or double bond as needed to satisfy valence requirements. R¹ is halo, aliphatic, heteroaliphatic, alicyclic, heteroalicyclic, aryl, heteroaryl, —OR$^a$, —SR$^a$, —COOR$^a$, or —N(R$^a$)$_2$, and R² is —OR$^a$, —SR$^a$, alicyclic, heteroalicyclic, aryl, or heteroaryl; or R¹ and R² together are =O or =S. Each R³ independently is aliphatic, heteroaliphatic, aryl, heteroaryl, —COOR$^a$, or —C(O)N(R$^a$)$_2$; and m is 0, 1, or 2. R⁴ and R⁵ independently are hydrogen, aliphatic, heteroaliphatic, halo, —OR$^a$, —SR$^a$, oxygen, or sulfur, or R⁴ and R⁵ together with the carbon atoms to which they are bound define ring B where ring B is aryl, heteroaryl, alicyclic, or heteroalicyclic. Each R$^a$ independently is hydrogen or alkyl. Unless expressly stated, each substituent may be unsubstituted or substituted if appropriate. As one non-limiting example, an aliphatic substituent may be substituted aliphatic, e.g., haloalkyl. In some embodiments, the compound according to Formula I is not a naturally occurring compound. In particular embodiments, the compound according to Formula I is not eudistidine A, eudistidine B, or eudistidine C. In certain embodiments, m is 0.

In some embodiments, R⁴ and R⁵ together with the carbon atoms to which they are bound define an optionally substituted phenyl ring, and the eudistidine has a chemical structure according to Formula II:

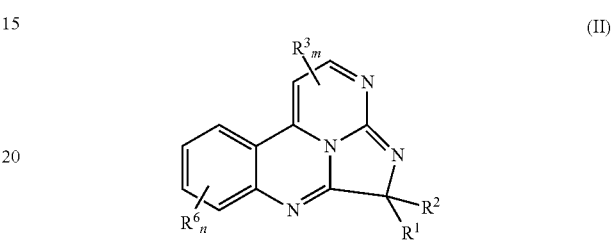

(II)

wherein n is 0, 1, 2, 3, or 4; and each R⁶ independently is aliphatic, heteroaliphatic, alicyclic, heteroalicyclic, aryl, heteroaryl, halo, —OR$^a$, —SR$^a$, —COOR$^a$, or —C(O)N(R$^a$)$_2$, where each R$^a$ independently is hydrogen or alkyl. R¹-R³ and m are as defined above. In some embodiments, m is 0, n is 0, or m and n are 0.

In any of the above embodiments, R¹ may be hydroxyl, lower alkoxy, lower aliphatic, alicyclic, or aryl. In some embodiments, R¹ is hydroxyl, lower alkoxy, optionally substituted lower aliphatic, optionally substituted phenyl, optionally substituted imidazolyl, optionally substituted indolyl, optionally substituted pyrrolyl, optionally substituted pyrazolyl, optionally substituted pyridyl, optionally substituted furyl, optionally substituted naphthyl, or optionally substituted cyclohexyl. Exemplary R¹ groups include, but are not limited to:

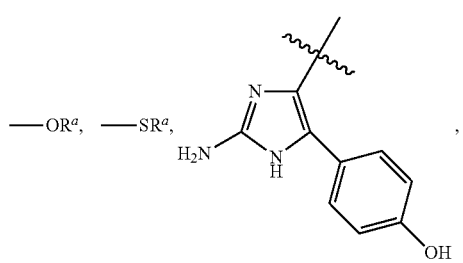

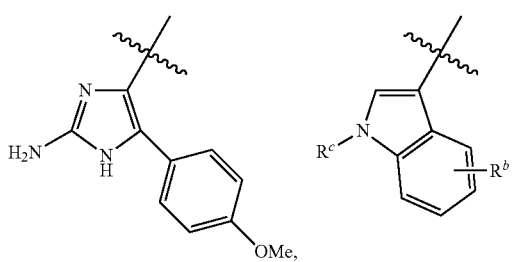

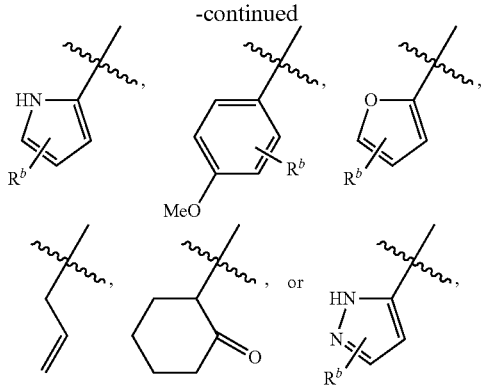

wherein $R^b$ is hydrogen, halo, aliphatic, heteroaliphatic, —$OR^a$, —$SR^a$, —$C(O)OR^a$, or —$C(O)N(R^a)_2$; and $R^c$ is hydrogen, aliphatic, or heteroaliphatic. In some embodiments, $R^b$ is hydrogen, halo, lower alkyl, lower alkoxy, —COOH, —$C(O)OR^a$, or —$C(O)N(R^a)_2$ where each $R^a$ independently is hydrogen or lower alkyl, and $R^c$ is hydrogen or lower alkyl.

In any of the above embodiments, $R^2$ may be aryl or heteroaryl, such as monocyclic or bicyclic aryl, or monocyclic or bicyclic heteroaryl. Exemplary $R^2$ aryl groups include, but are not limited to, optionally substituted phenyl, optionally substituted naphthyl, and optionally substituted pyridyl. In an independent embodiment, $R^2$ is ortho or para substituted aryl, such as phenyl ortho or para substituted with hydroxyl, alkyl, alkoxy, or aryl. For example, $R^2$ may be phenyl ortho or para substituted with hydroxyl, lower alkyl, lower haloalkyl (e.g., —$CF_3$), lower alkoxy (e.g., methoxy), amido, or phenyl para substituted with optionally substituted phenyl. Exemplary $R^2$ groups include, but are not limited to:

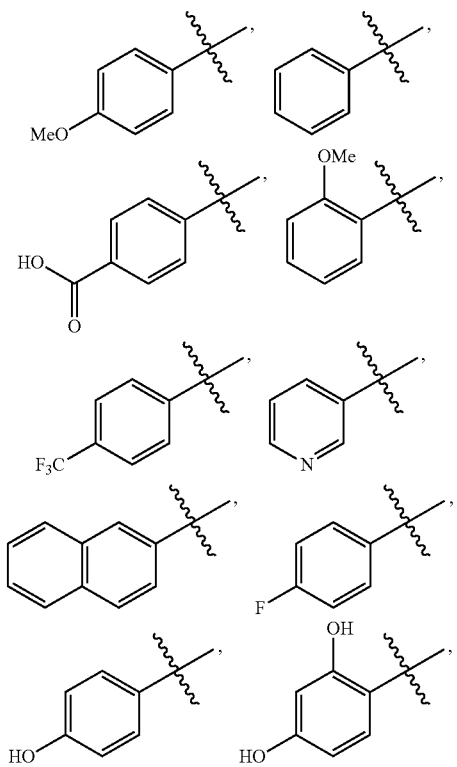

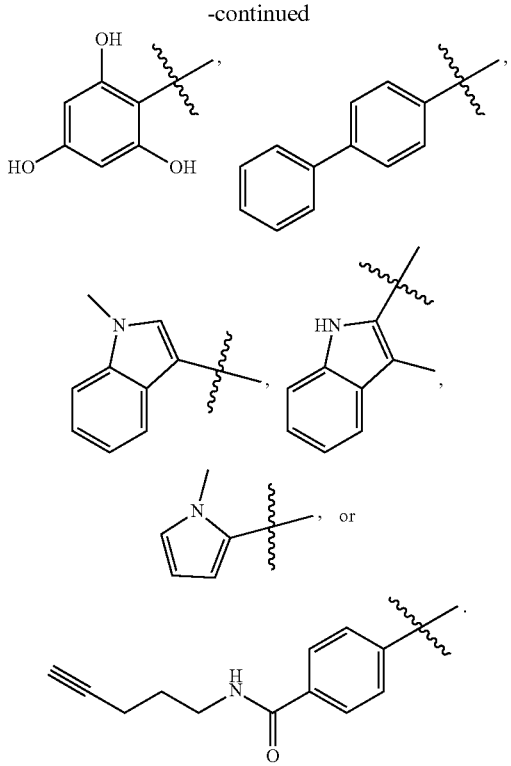

In some embodiments, the compound has a formula:

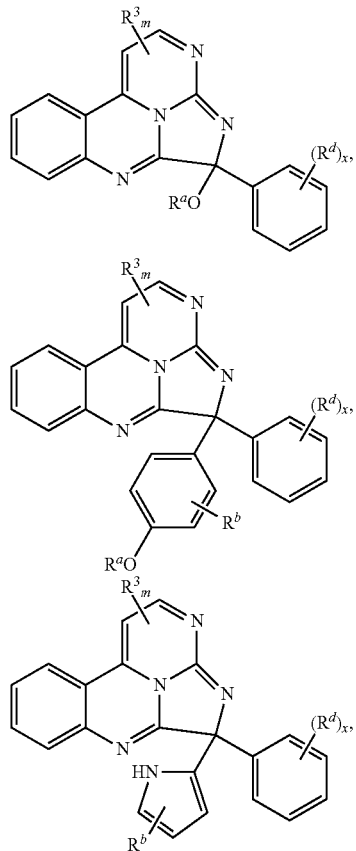

-continued

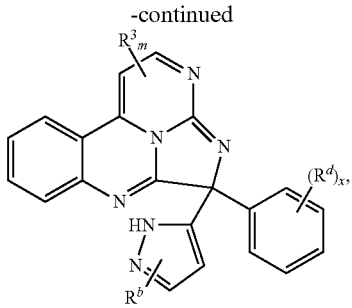

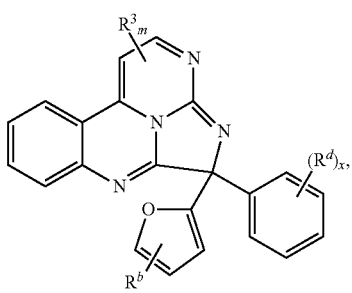

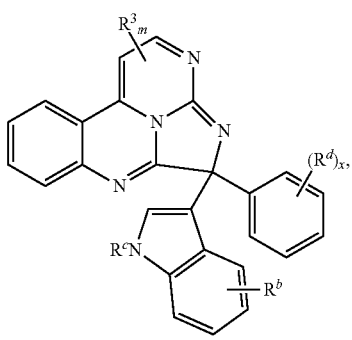

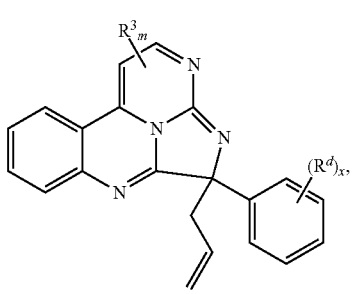

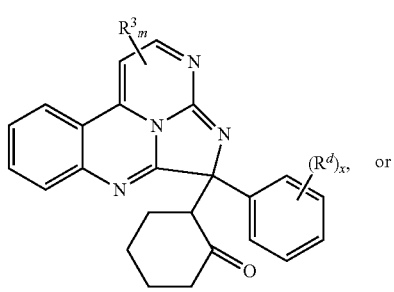 or

-continued

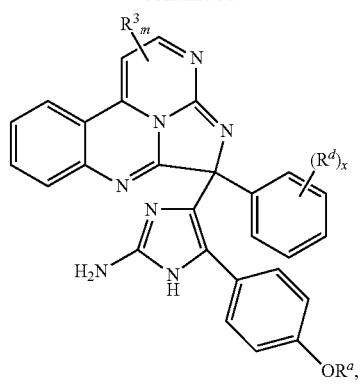

wherein $R^b$ is hydrogen, halo, aliphatic, heteroaliphatic, —$OR^a$, —$SR^a$, —$C(O)OR^a$, or —$C(O)N(R^a)_2$; $R^c$ is hydrogen, aliphatic, or heteroaliphatic; each $R^d$ independently is hydroxyl, halo, aliphatic, heteroaliphatic, amido, —$OR^a$, —$SR^a$, or aryl; and x is 0, 1, 2, or 3. In some embodiments, m is 0. In certain embodiments, $R^a$ is H or methyl.

Exemplary eudistidines are shown in Table 1.

TABLE 1

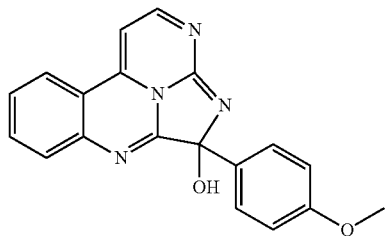

eudistidine A

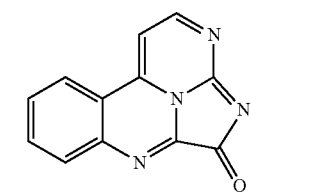

eudistidine B

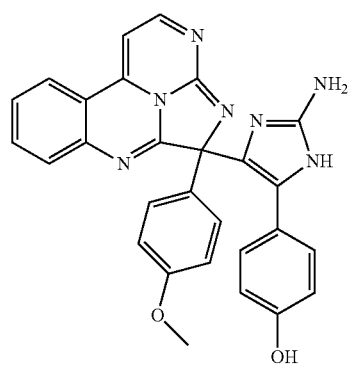

eudistidine C

TABLE 1-continued
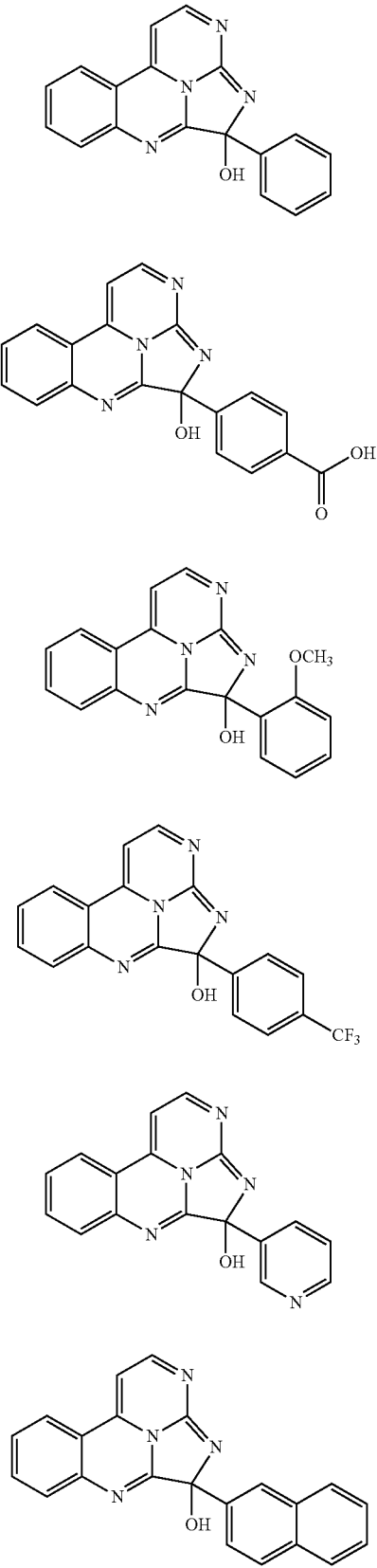
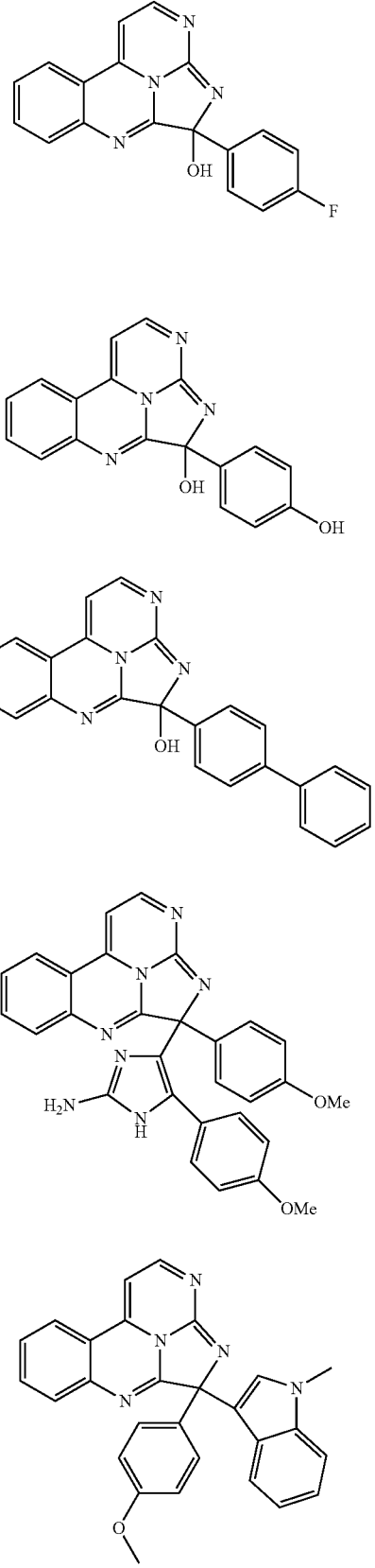

TABLE 1-continued
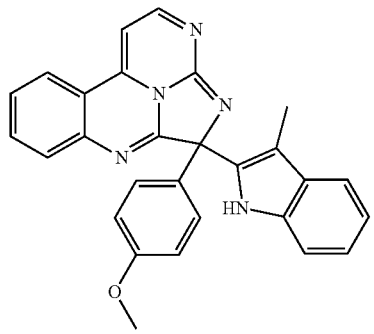 [SMILES: COc1ccc(C2(c3[nH]c4ccccc4c3C)N=C3N=CC=C4c5ccccc5N=C2N43)cc1]
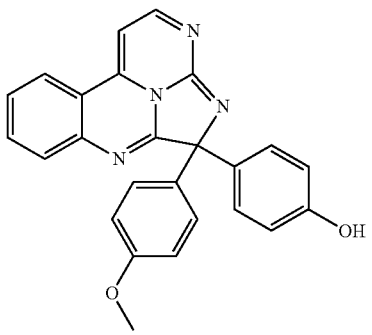
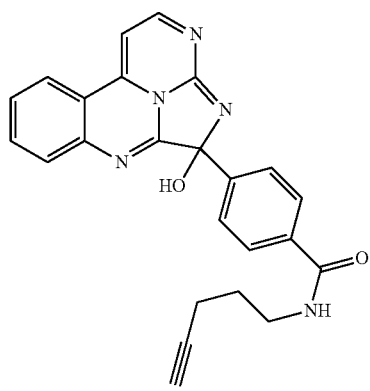 [SMILES: C#CCCCNC(=O)c1ccc(C2(O)N=C3N=CC=C4c5ccccc5N=C2N43)cc1]
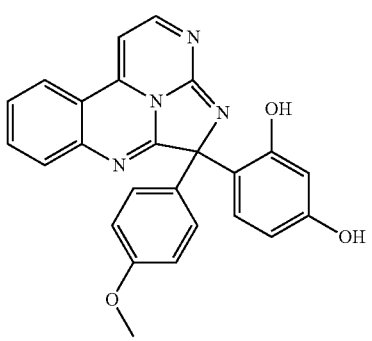
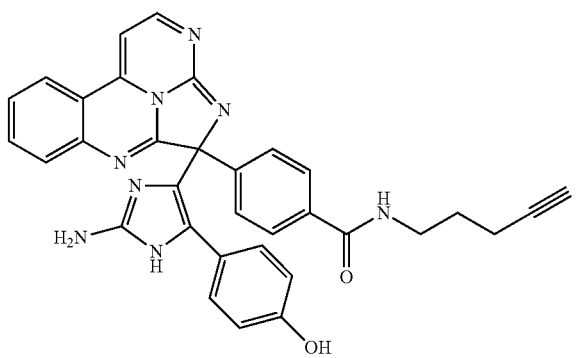 [SMILES: C#CCCCNC(=O)c1ccc(C2(c3nc(N)[nH]c3-c3ccc(O)cc3)N=C3N=CC=C4c5ccccc5N=C2N43)cc1]
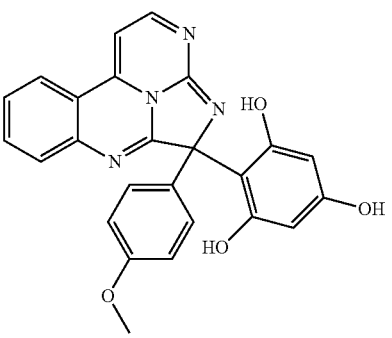
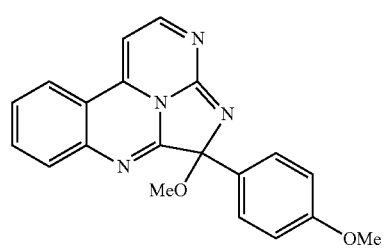 [SMILES: COc1ccc(C2(OC)N=C3N=CC=C4c5ccccc5N=C2N43)cc1]
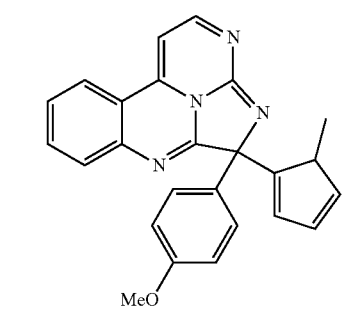 [SMILES: COc1ccc(C2(C3=CC=CC3C)N=C3N=CC=C4c5ccccc5N=C2N43)cc1]

TABLE 1-continued

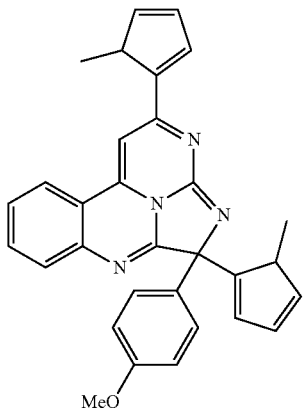 [SMILES: COc1ccc(C2(C3=CC=CC3C)N=C3N=C(C4=CC=CC4C)C=C4c5ccccc5N=C2N43)cc1]

III. SYNTHESIS

A general retrosynthetic approach to synthesizing eudistidine A and eudistidine B is outlined in Scheme 1 (FIG. 1). Eudistidine A (1) is synthesized in a four-step sequence featuring a condensation/cyclization reaction cascade between 4-(2-aminophenyl)pyrimidin-2-amine (4) and 4-methoxy-phenylglyoxal (5), while the synthesis of eudistidine B (2) was accomplished in a similar fashion with glyoxylic acid (6) in place of 5 (FIG. 2).

Precursor 4-(2-aminophenyl)pyrimidin-2-amine (4), is synthesized in three steps from 1-(2-nitrophenyl)ethanone as reported previously (Agarwal et al., *Tetrahedon* 2009, 65:1153-1161), but with a slight modification at the last step. Specifically Pd/C is used to hydrogenate 4-(2-nitrophenyl) pyrimidin-2-amine, instead of HCl and iron. Compound 4 provides rings A and B and all four nitrogen atoms of the eudistidine compounds.

Aryl glyoxal 5 is prepared by oxidizing 2-bromo-4'-methoxyacetophenone. Compounds 4 and 5 are condensed and cyclized, followed by oxidation to form eudistidine A (1). Suitable oxidants include, but are not limited to, iodine, DDQ (2,3-dichloro-5,6-dicyano-1,4-benzoquinone), $MnO_2$, and $Fe^{3+}$ salts. In some embodiments, the oxidant is iodine.

Figure 2:
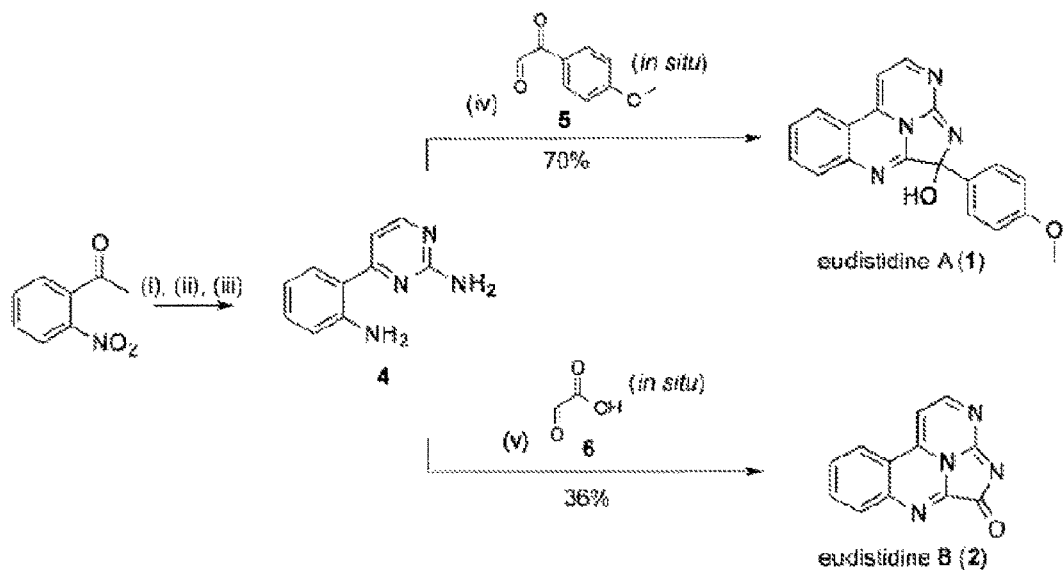
FIG. 2 is a synthetic scheme for preparation of eudistidines A (1) and B (2). Reagents and conditions: (i) DMSO, $H_2O$, 65° C., 3 h; 12, 60° C., 1 h; (ii) DMF, 60° C., 18 h.

Eudistidine B (2) is similarly synthesized by condensation of compound 4 with glyoxylic acid (6) (FIG. 2). No oxidant is needed. Eudistidine C (3) is synthesized by maintaining a solution of eudistidine A with 4-(2-amino-1H-imidazol-5-yl)phenol in trifluoroacetic acid for an effective period of time, e.g., for 36 hours. Other analogs can be synthesized in a similar manner; TFA can be replaced with other reagents that produce related conditions.

Embodiments of the disclosed eudistidine analogs can be synthesized in four steps. A solution comprising compound A is heated with 1,1-dimethoxy-N,N'-dimethylmethanamine at an effective temperature for an effective period of time to form an intermediate.

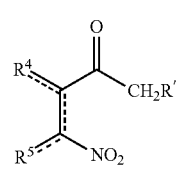

(A)

With respect to compound A, R' is hydrogen or $R^3$, where $R^3$-$R^5$ are as defined previously. In some examples, compound A is heated neat with 1,1-dimethoxy-N,N'-dimethyl-methan-amine at a temperature of 100-110° C. for 2-4 hours, such as at 105° C. for 3 hours, to form the intermediate. The intermediate may be combined with a solvent, such as dichloromethane, and purified, e.g., by $SiO_2$ chromatography with elution using a gradient of 50-100% ethyl acetate in hexanes.

The intermediate is refluxed with guanidine hydrochloride for an effective period of time to form compound B. In some embodiments the intermediate is combined with potassium carbonate and guanidine hydrochloride in ethanol and refluxed overnight. The refluxed solution may be concentrated, dissolved in ethyl acetate and water, and extracted with ethyl acetate. The ethyl acetate extracts are combined, filtered, and concentrated to provide compound B.

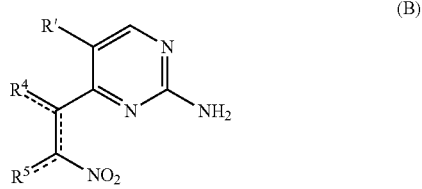

(B)

A solution comprising compound B is hydrogenated with a catalyst. e.g., a catalyst comprising Pd/C, to form compound C. In some examples, compound B is dissolved in a 1:1 solution of ethanol-ethyl acetate, Pd/C is added, and the solution is allowed to stir for an effective period of time (e.g., overnight) under a hydrogen atmosphere. The suspension is filtered, and the filtrate is dried to provide compound C.

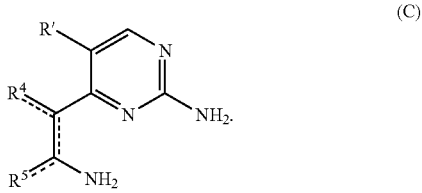

(C)

$R^2$—C(O)$CH_2$X (X is halo) is oxidized to form $R^2$—C(O)C(O)H. In some embodiments, a Kornblum oxidation in a solvent comprising dimethyl sulfoxide is performed to produce a glyoxal. The oxidation reaction is performed at an effective temperature for an effective period of time to form the glyoxal. In some examples, oxidation is carried out at 50-75° C. for 2-5 hours, such as at 65° C. for 3 hours.

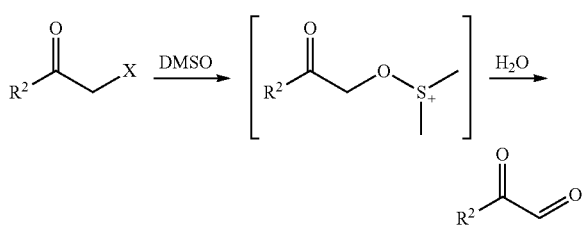

In certain embodiments, X is bromo.
When $R^2$ is —OH or —SH, compound C is heated with HOC(O)C(O)H or HSC(O)C(O)H for an effective period of time to form compound D where A is O or S (e.g., eudistidine B or an analog thereof). In some examples, a solution comprising compound C in dimethylformamide is heated with HOC(O)C(O)H or HSC(O)C(O)H at 50-70° C. for several hours, such as at 60° C. overnight. Compound D may be purified by any suitable means, e.g., by reversed phase flash chromatography.

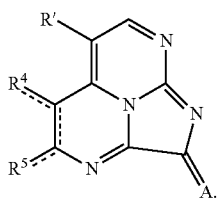

(D)

In embodiments where $R^2$ is other than —OH or —SH, the glyoxal is heated with compound C at an effective temperature for an effective period of time, followed by addition of an oxidant to form compound E. In some embodiments, the glyoxal is added dropwise to a chilled solution (e.g., at 0° C.) comprising compound C. After addition of the glyoxal, the solution may be heated (e.g., at 50-70° C.) for a period of time (e.g., 15-60 minutes), such as at 60° C. for 30 minutes. An oxidant is subsequently added, and heating is continued for an additional period of time, e.g., 30 minutes to 2 hours, to form compound E. In some examples, the oxidant is iodine and heating is continued at 60° C. for an additional one hour. Compound E may be purified by any suitable means, e.g., by reversed-phase HPLC.

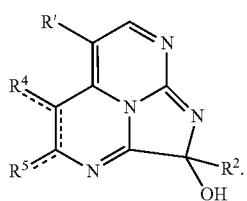

(E)

In some embodiments, compound E is further reacted with a nucleophile comprising $R^1$ at an effective temperature for an effective period of time to form compound F. The nucleophile may be $R^1H$ or $R^1$-LG where LG is an effective leaving group, e.g., a weak base. For example, when $R^1$ is an allyl group, $R^1$-LG may be $H_2C$=CH—$CH_2$—$Si(CH_3)_3$. In certain examples, a solution comprising compound E (e.g., eudistidine A or an analog thereof) in neat TFA, or in DMSO-5% aqueous trifluoroacetic acid, is mixed with $R^1H$ at a temperature of 20-70° C. for several hours to several days, e.g., at 25° C. for 36 hours, to form compound F (e.g., eudistidine C or an analog thereof).

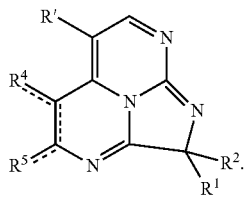

(F)

In some embodiments, the open position on the pyrimidine ring can be substituted with $R^3$ using a cross-coupling reaction, as will be understood by those skilled in the art of organic compound synthesis.

Pharmaceutically acceptable salts of the disclosed eudistidines can be prepared by conventional means as will be understood by one of ordinary skill in the art of organic compound synthesis. In some embodiments, a eudistidine is treated with hydrochloric acid, trifluoroacetic acid, or acetic acid to form the corresponding acid addition salt.

IV. PHARMACEUTICAL COMPOSITIONS AND METHODS OF USE

Another aspect of the disclosure includes pharmaceutical compositions prepared for administration to a subject and which include a therapeutically effective amount of one or more of the currently disclosed eudistidines (including pharmaceutically acceptable salts thereof). In some embodiments, the pharmaceutical composition comprises a synthetic eudistidine analog or pharmaceutically acceptable salt thereof. The therapeutically effective amount of a disclosed eudistidine will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed eudistidines is understood by those of skill in the art. Pharmaceutical compositions comprising embodiments of the disclosed eudistidines may comprise a single active ingredient (e.g., a naturally occurring eudistidine or eudistidine analog), or may comprise plural active ingredients.

Pharmaceutical compositions comprising the disclosed eudistidines may be manufactured by means of conventional mixing, dissolving, granulating, dragee-making levigating, emulsifying, encapsulating, entrapping or lyophilization processes. Pharmaceutical compositions for administration to a subject can include carriers, thickeners, diluents, buffers, preservatives, surface active agents and the like in addition to the eudistidine(s). The pharmaceutical compositions comprising one or more naturally occurring or synthetic eudistidines may be formulated in a variety of ways depending, for example, on the mode of administration and/or on the location and type of disease to be treated.

A suitable administration format may best be determined by a medical practitioner for each subject individually. Various pharmaceutically acceptable carriers (including non-naturally occurring carriers) and their formulation are described in standard formulation treatises, for example, Remington's Pharmaceutical Sciences by E. W. Martin. See also Wang and Hanson, J. Parenteral Sci. Technol., 10(Supp. 42): 2S, 1988. A non-naturally occurring carrier can include synthetic liposomes, microspheres made of biodegradable polymers such as polyglycolic acids, or synthetic microspheres of natural materials such as albumen. Examples of other non-naturally occurring carriers are synthetics polymers, protein conjugates, virosomes, dendrimers, and nanofibers. In another example, the carrier may be present in a concentration that does not occur in nature.

The dosage form of the pharmaceutical composition will be determined by the mode of administration chosen. For instance, in addition to injectable fluids, inhalational, topical, ophthalmic, peritoneal, and oral formulations can be employed. Inhalational preparations can include aerosols, particulates, and the like. In general, the goal for particle size for inhalation is about 1 µm or less in order that the pharmaceutical reach the alveolar region of the lung for absorption. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The compositions or pharmaceutical compositions can be administered by any route, including parenteral administration, for example, intravenous, intramuscular, intraperitoneal, or intra-articular injection or infusion, or by sublingual, oral, topical, intranasal, ophthalmic, or transmucosal administration, or by pulmonary inhalation. When the active compounds are provided as parenteral compositions, for example, for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or depot slow release preparation may be used so that therapeutically effective amounts of the preparation are delivered into the bloodstream over many hours or days following transdermal injection or delivery.

Eudistidines are also suitably administered by sustained-release systems. Suitable examples of sustained-release formulations include suitable polymeric materials (such as, for example, semi-permeable polymer matrices in the form of shaped articles, for example, films, or mirocapsules), suitable hydrophobic materials (for example as an emulsion in an acceptable oil) or ion exchange resins, and sparingly soluble derivatives (such as, for example, a sparingly soluble salt). Sustained-release compounds may be administered by intravascular, intravenous, intra-arterial, intramuscular, subcutaneous, intra-pericardial, or intra-coronary injection. Administration can also be oral, rectal, parenteral, intracisternal, intravaginal, intraperitoneal, topical (as by powders, ointments, gels, drops or transdermal patch), buccal, or as an oral or nasal spray.

Preparations for administration can be suitably formulated to give controlled release of the eudistidine(s). For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance, as in a unit dosage form of the active substance. See, for example, U.S. Pat. No. 5,700,486.

In some embodiments, eudistidine(s) are delivered by way of a pump (see Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution may also be employed. The key factor in selecting an appropriate dose is the result obtained, as measured by increases or decreases in HIF-1 activation, or by other criteria for measuring control or prevention of disease, as are deemed appropriate by the practitioner. Other controlled release systems are discussed in the review by Langer (*Science* 249:1527-1533, 1990).

In another aspect of the disclosure, eudistidine(s) are delivered by way of an implanted pump, described, for example, in U.S. Pat. No. 6,436,091; 5,939,380; and 5,993,414. Implantable drug infusion devices are used to provide subjects with a constant and long term dosage or infusion of a drug or any other therapeutic agent. Essentially, such device may be categorized as either active or passive.

Active drug or programmable infusion devices feature a pump or a metering system to deliver the drug into the patient's system. An example of such an active drug infusion device currently available is the Medtronic SynchroMed™ programmable pump. Such pumps typically include a drug reservoir, a peristaltic pump to pump the drug out from the reservoir, and a catheter port to transport the pumped out drug from the reservoir via the pump to a patient's anatomy. Such devices also typically include a battery to power the pump, as well as an electronic module to control the flow rate of the pump. The Medtronic SynchroMed™ pump further includes an antenna to permit the remote programming of the pump.

Passive drug infusion devices, in contrast, do not feature a pump, but rather rely upon a pressurized drug reservoir to deliver the drug. Thus, such devices tend to be both smaller as well as cheaper as compared to active devices. An example of such a device includes the Medtronic IsoMed™. This device delivers the drug into the patient through the force provided by a pressurized reservoir applied across a flow control unit.

The implanted pump can be completely implanted under the skin of a subject, thereby negating the need for a percutaneous catheter. These implanted pumps can provide the patient with eudistidine(s) at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump system. Osmotic pumps may be much smaller than other constant rate or programmable pumps, because their infusion rate can be very low. An example of such a pump is described listed in U.S. Pat. No. 5,728,396.

The eudistidines may also be delivered passively and in sustained fashion as part of and incorporated into implantable devices, such as vascular stents which can be placed directly into diseased blood vessels through several standard approaches, including direct surgical insertion or percutaneously with angiographic control.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, the eudistidines according to the present disclosure are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

For topical administration, the eudistidines can be, for example, mixed with a liquid delivery agent for administration locally. The eudistidines are readily suspendable in water and saline, and as such these would be useful for delivery since water or saline do not cause adverse biological tissue effects. This allows sufficiently high doses to be administered locally or systemically, without secondary toxicity from the delivery vehicle. However, even when suspended in water or saline, the drug may be supplied via a unit dosage form such as a vial or syringe. Lyophilized forms of the drug can also be supplied for subsequent solubilization or suspension in water, saline, or other suitable vehicle.

Pharmaceutical compositions that comprise at least one eudistidine as described herein as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, eudistidine(s) can be formulated generally by mixing them at the desired degree of purity, in a unit dosage injectable form (solution, suspension, or emulsion), with a pharmaceutically acceptable carrier, for instance, one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the eudistidine(s) each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise at least one eudistidine, in some embodiments, will be formulated in unit dosage form, suitable for individual administration of precise dosages. The amount of eudistidine(s) administered will be dependent on the subject being treated, the severity of the affliction, and the manner of administration, and is best left to the judgment of the prescribing clinician. Within these bounds, the formulation to be administered will contain a quantity of the eudistidine(s) in amounts effective to achieve the desired effect in the subject being treated.

The therapeutically effective amount of eudistidine will be dependent on the particular eudistidine utilized, the subject being treated, the severity and type of the affliction, and the manner of administration. The exact dose is readily determined by one of skill in the art based on the potency of the specific compound, the age, weight, sex and physiological condition of the subject.

Embodiments of the disclosed pharmaceutical compositions may include a therapeutically effective amount of a second therapeutic agent other than the eudistidine(s). The second therapeutic may increase the effectiveness of the pharmaceutical composition relative to a pharmaceutical composition comprising only a eudistidine as an active agent. Exemplary classes of second therapeutic agents include, but are not limited to, anticancer agents, antimalarial agents, antihistamines, antibiotics, antiviral medications, anti-inflammatory agents, and combinations thereof.

In some embodiments, the second therapeutic agent is an anticancer agent. Suitable anticancer agents include, but are not limited to, chemotherapeutic drug treatment, radiation, gene therapy, hormonal manipulation, immunotherapy and antisense oligonucleotide therapy. Chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and bbr3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as *podophyllum* (for example, etoposide, and teniposide), taxane (for example, docetaxel and paclitaxel), *vinca* (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, hydroxyurea, and mitomycin; topoisomerase inhibitors, such as topotecan and irinotecan; monoclonal antibodies, such as alemtuzumab, bevacizumab, cetuximab, gemtuzumab, rituximab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin. Co-administration of the disclosed eudistidines with radiation therapy is also contemplated. Methods for treating cancers using radiation therapy are well known in the art.

In other embodiments, the second therapeutic agent is an antimalarial agent. Suitable antimalarial agents include, but are not limited to, quinine, quinidine, cinchoine, cinchonidine, 4-aminoquinolones such as amodiaquine, chloroquine, chloroquine analogs, quinoline analogs, hydroxychloroquine, pyrimethamine, chloroguanide (proguanil), atovaquone (available as Malarone, a combination of atovaquone and proguanil), sulfonamides such as sulfadoxine and sulfamehtoxypyridazine, mefloquine, primaquine, artemisinin, artemisinin derivatives such as artesunate, artemether, arteether, and dihydroartemisinin, halofantrine (a phenanthrene methanol), Halfan, doxycycline, tetracycline, clindamycin, prodiginines, and combinations thereof.

In still other embodiments, the second therapeutic agent is an anti-inflammatory agent. Exemplary anti-inflammatory agents include non-steroidal anti-inflammatory drugs (NSAIDs) such as ibuprofen, ketoprofen, piroxicam, naproxen, sulindac, aspirin, choline subsalicylate, diflunisal, fenoprofen, indomethacin, meclofenamate, salsalate, tolmetin, ketorolac, flurbiprofen, and magnesium salicylate.

Embodiments of a method for using the disclosed eudistidines comprise inhibiting hypoxia-inducible factor 1 activity by contacting a cell with an effective amount of a eudistidine (including pharmaceutically acceptable salts thereof). The cell may be contacted in vitro or in vivo with the eudistidine. The cell also may be contacted with a second therapeutic agent. In some embodiments, contacting the cell comprises administering to a subject a therapeutically effective amount of (i) the compound or pharmaceutically acceptable salt thereof, or (ii) a pharmaceutical composition comprising the compound or pharmaceutically acceptable salt thereof and at least one pharmaceutically acceptable carrier.

Embodiments of the disclosed eudistidines (including pharmaceutically acceptable salts thereof) and/or pharmaceutical compositions thereof may be administered to a subject having, or suspected of having, a condition mediated by hypoxia. In particular, embodiments of the disclosed eudistidines and/or pharmaceutical compositions may be administered to treat or ameliorate conditions in which hypoxia is mediated by HIF-1.

Since hypoxia is a hallmark of cancer, in particular solid tumors that include (but are not limited to) colorectal cancer, lung, renal, cervical, ovarian, hepatocellular and prostate cancer, embodiments of the disclosed compounds may be an effective treatment targeting neovascularization and tumor hypoxia of solid tumors as well as other HIF-related diseases including, but not limited to, inflammatory diseases and malaria. Some embodiments of the disclosed compounds may inhibit HIF-1 activation in tumors, increase sensitivity of tumor cells to radiation and/or chemotherapy, and/or inhibit inflammatory responses. A eudistidine or a pharmaceutical composition thereof may be formulated for use in human and/or veterinary medicine, and a therapeutically effective amount of the eudistidine or pharmaceutical composition thereof may be administered to a subject having, or suspected of having, a tumor, particularly a solid tumor. In some embodiments, subjects are selected using specific criteria, such as a definitive diagnosis of a solid tumor based on, for example, radiological data, histological data, and/or biopsy results. In some embodiments, the eudistidine or pharmaceutical composition may be administered directly as part of a surgical procedure, or at the bedside by a treating clinician. The eudistidine can be diluted for instance in a pharmaceutically acceptable solvent and given by injection using sterile syringes and small bore needles (25 gauge and less) to a tumor site. Alternatively, a wound bed can be irrigated for instance with a therapeutically effective solution containing a known concentration (dosage) of a eudistidine. Precise control and localization of therapeutic effects can thus be obtained.

Some embodiments of the disclosed eudistidines and pharmaceutical compositions thereof are capable of reducing parasitemia by inhibiting HIF-1 activation. In particular, certain embodiments of the disclosed compounds and pharmaceutical compositions thereof have an antiplasmodial effect. A eudistidine or a pharmaceutical composition thereof may be formulated for use in human and/or veterinary medicine, and a therapeutically effective amount of the eudistidine or pharmaceutical composition thereof may be administered to a subject infected with, or suspected of being infected with, a *Plasmodium* species. Over two hundred *Plasmodium* species are known, and new species continue to be discovered. Exemplary *Plasmodium* species capable of infecting humans include *P. falciparum, P. knowlesi, P. malariae, P. ovale*, and *P. vivax. P. berghei, P. chabaudi, P. yoelii* and *P. vinckei* have been used to study malarial infections in the laboratory. In some embodiments, subjects are selected using specific criteria, such as a definitive diagnosis of a malarial infection based on, for example, clinical signs and symptoms and/or laboratory evidence of malarial infection. An example of such a subject would be a person in whom positive blood cultures have identified a *Plasmodium* species parasite. In some examples, the drug is administered to a subject from whom a *Plasmodium* species parasite has been obtained (such as by obtaining, e.g., a blood sample) and cultured, and the *Plasmodium* species parasite has been demonstrated in culture to be inhibited by (i.e., sensitive to) the eudistidine.

Some embodiments of the disclosed eudistidines and pharmaceutical compositions thereof are capable of reducing inflammation by inhibiting HIF-1 activation. In particular, certain embodiments of the disclosed eudistidines and pharmaceutical compositions thereof have an anti-inflammatory effect. A eudistidine or a pharmaceutical composition thereof may be formulated for use in human and/or veterinary medicine, and a therapeutically effective amount of the eudistidine or pharmaceutical composition thereof may be administered to a subject having, or suspected of having, a condition that produces an inflammatory response mediated by hypoxia. Exemplary conditions that produce an inflammatory response mediated by hypoxia include without limitation malignant tumors, intestinal inflammation (e.g., inflammatory bowel disease), lung inflammation (e.g., resulting from acute lung injury), ischemia, atherosclerosis, myocardial infarction, rheumatoid arthritis, and wound healing. In some embodiments, subjects are selected using specific criteria, such as a definitive diagnosis of an inflammatory condition mediated by hypoxia based on, for example, clinical signs and symptoms and/or laboratory evidence of inflammation. An example of such a subject would be a person having an elevated C-reactive protein level.

With respect to tumors, efficacy of the treatment is shown, for example, by a regression of symptoms, for example reduction of tumor size, reduction of metastasis, reduction of recurrence of cancer, or any other measurable return to or towards a system more characteristic of health (for instance, changes in gene expression to be more like a healthy profile and less like a cancerous profile). With respect to malaria, efficacy of the treatment is shown, for example, by regression of symptoms (e.g., fever, chills, headache, sweats, fatigue, nausea and vomiting) and/or decrease of parasite load. With respect to inflammation, efficacy of the treatment is shown, for example, by regression of symptoms (for example, redness (e.g., surrounding a wound), heat, swelling, fatigue, persistent pain, and/or loss of function) and/or reduction in one or more inflammation biomarkers (e.g., erythrocyte sedimentation rate and/or elevated levels of C-reactive protein, homocysteine, ferritin, HDL (high-density lipoprotein), monocytes, and/or blood glucose).

The disclosed eudistidines will generally be used in an amount effective to achieve the intended result, for example in an amount effective to treat or prevent the particular disease being treated. The eudistidine(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a eudistidine to a patient suffering from malaria provides therapeutic benefit not only when the underlying infection is eradicated or ameliorated, but also when the patient reports a decrease in the severity or duration of the symptoms associated with the malarial infection. As another example, therapeutic benefit in the context of inflammation includes an improvement a reduction in symptoms of inflammation and/or a normalization of one or more inflammation biomarkers. Therapeutic benefit also includes halting or slowing the progression of the disease, e.g., a solid tumor, regardless of whether improvement is realized.

The amount of eudistidine administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an $IC_{50}$ of the particular compound as measured in an in vitro assay, such as the in vitro HIF-1α/p300 binding inhibition assays described in the Examples section. In some embodiments, an initial dosage for use in animals may be formulated to achieve a circulating blood or serum concentration of active compound that is at least 25 µM, such as at least 50 µM or at least 75 µM, or a circulating blood or serum concentration from 25 µM to 300 µM, from 50 µM to 250 µM, from 75 µM to 200 µM, or from 75 µM to 150 µM. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, Chapter 1, pp. 1 46, latest edition, Pagamonon Press, and the references cited therein.

Initial dosages can also be estimated from in vivo data, such as animal models. Animal models useful for testing the efficacy of compounds to treat or prevent the various diseases described above are well-known in the art. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but may be higher or lower, depending upon, among other factors, the activity of the eudistidine, its bioavailability, the mode of administration and various factors discussed above. In some embodiments, a therapeutically effective dose is 0.01 mg/kg/day to 100 mg/kg/day, such as 0.1-100 mg/kg/day, 1-50 mg/kg/day, 1-25 mg/kg/day, or 1-10 mg/kg/day. The dosage is best left to the judgment of the prescribing clinician. Dosage amount and interval may be adjusted individually to provide plasma levels of the eudistidine(s) which are sufficient to maintain therapeutic or prophylactic effect. For example, the eudistidines may be administered once per week, several times per week (e.g., every other day), once per day or multiple times per day, depending upon, among other things, the mode of administration, the specific indication being treated and the judgment of the prescribing clinician. In cases of local administration or selective uptake, such as local topical administration, the effective local concentration of eudistidine(s) may not be related to plasma concentration. Skilled artisans will be able to optimize effective local dosages without undue experimentation.

Preferably, the eudistidine(s) will provide therapeutic or prophylactic benefit without causing substantial toxicity. Toxicity of the eudistidine(s) may be determined using standard pharmaceutical procedures. The dose ratio between toxic and therapeutic (or prophylactic) effect is the therapeutic index. Eudistidine(s) that exhibit high therapeutic indices are preferred.

A therapeutically effective amount of a eudistidine can be administered in a single dose, or in multiple doses, for example daily, weekly, every two weeks, or monthly during a course of treatment. Additionally, the eudistidine may be incorporated into or onto implantable constructs or devices, such as vascular stents, for sustained regional or local release.

In some embodiments, a second therapeutic agent is administered to the subject. In certain embodiments, the second therapeutic agent is an anticancer agent, an antimalarial agent, or an anti-inflammatory agent. The second therapeutic agent may enhance or increase the effectiveness of a eudistidine. For example, administering both a eudistidine and a second therapeutic agent may be more effective than administering only a eudistidine. In such embodiments, the eudistidine and second therapeutic agent can be delivered at the same time (such as part of the same composition or as separate compositions), or can be administered at different times. When administered at different times, the second therapeutic agent can either be administered before the eudistidine or after the eudistidine. The time between administration of the eudistidine and the second therapeutic agent can vary and will depend on the type of second therapeutic agent selected, the disease or condition being treated, and/or the subject being treated. The second therapeutic agent can be administered in a single dose or in multiple doses. One of skill in the art can determine an appropriate dosing schedule for each subject.

The following examples are provided to illustrate certain particular features and/or embodiments. These examples should not be construed to limit the invention to the particular features or embodiments described.

V. EXAMPLES

General Procedures.

NMR spectra were obtained with a Bruker Avance III NMR spectrometer equipped with a 3 mm cryogenic probe and operating at 600 MHz for $^1$H and 150 MHz for $^{13}$C. $^1$H-$^{13}$C HMBC experiments were optimized for $^nJ$=8.3 Hz and $^1$H-$^{15}$N HMBC experiments were optimized for $^nJ$=8 Hz. (+)HRESIMS data were acquired on an Agilent Technology 6530 Accurate-mass Q-TOF LC/MS. Preparative reversed-phase HPLC was run on a Waters 2545 system using a Phenomenex Luna $C_{18}$ (10μ, 110 Å, 75×30 mm) column run with the indicated gradient.

Animal Material.

Specimens of the ascidian *Eudistoma* sp. were collected at a depth range of −3 to −10 m on the Koror side of the collapsed Koror-Babeldaob Bridge in the Koror/Airai Channel, Palau (07°21.64' N, 134°30.17' E) in September 1998 by Dr. Patrick Colin, under contract through the Coral Reef Research Foundation for the Natural Products Branch, National Cancer Institute. Taxonomic identification of the ascidian was done by Francoise Monniot and a voucher specimen (0CDN5649) was deposited at the Smithsonian Institute, Washington, D.C.

Example 1

Screening Assay

A high-throughput assay was developed based on the methodologies of Kung, et al. (*Cancer Cell* 2004, 6:33-43) to screen for compounds and natural product extracts that can disrupt CH1/C-TAD binding as a means of blocking HIF-1 activation and potentially inhibiting tumor response to hypoxic conditions. The screening assay employed the N-terminal biotinylated HIF-1α C-TAD domain (aa 786-826) bound to streptavidin-coated 384 well plates and a GST-labeled p300 CH1 domain (aa 323-423). Binding of soluble CH1 to the immobilized C-TAD was measured by the fluorescence of a europium-tagged anti-GST antibody. The CH1/C-TAD binding interaction is very strong, as it forms a highly ordered complex with 3,393 Å$^2$ of buried surface area (Freedman et al., *Proc. Natl. Acad. Sci. USA* 2002, 99:5367-5372).

The hit rate from a screen for small molecule inhibitors of this protein-protein interaction was anticipated to be very low. Prior screening of a library of 600,000 pure compounds using a similar CH1/C-TAD system provided only a single lead compound (Kung, et al., *Cancer Cell* 2004, 6:33-43). The NCI's Natural Products Repository, which contains extracts from taxonomically diverse terrestrial plants, marine invertebrates, and microbial isolates, was screened. Testing of >158,000 crude natural product extracts and prefractionated extract samples for inhibition of CH1/C-TAD binding identified 27 confirmed hits. One of these was a relatively polar fraction from the organic solvent extract of the colonial marine ascidian *Eudistoma* sp. collected in Palau that exhibited significant activity. Detailed chemical studies were initiated.

Example 2

Isolation, Purification, and Characterization of Eudistidines

The high-throughput screen for inhibitors of the protein binding domains of p300 (CH1) and HIF-1α (C-TAD) identified an extract of the marine ascidian *Eudistoma* sp. as active. The ascidian specimen (668 g, wet weight) was stored frozen until it was extracted according to the procedures detailed by McCloud (*Molecules* 2010, 15:4526-4563) to give 7.2 g of organic solvent ($CH_2Cl_2$-MeOH, 1:1) extract. A portion of the organic extract (914.4 mg) was fractionated on two diol SPE cartridges (2 g) eluting with 9:1 hexane-$CH_2Cl_2$ (fraction A), 20:1 $CH_2Cl_2$-EtOAc (fraction B), 100% EtOAc (fraction C), 5:1 EtOAc-MeOH (fraction D), and 100% MeOH (fraction E) in a stepwise manner Repeated size exclusion Sephadex LH-20 column chromatography of fraction D (113.9 mg) using MeOH as the eluent yielded eudistidine A (1, 4.3 mg, 0.47%). Additional organic extract (1006.9 mg) was subjected to diol SPE chromatography and separated into five fractions as outlined above. A portion of fraction D (121.6 mg) was subjected to repeated size exclusion LH-20 column chromatography using 1:1 $CH_2Cl_2$-MeOH and 100% MeOH to give eudistidine B (2, 0.5 mg, 0.05%). Repeated size exclusion LH-20 column chromatography of fraction E (485.0 mg) using MeOH as the eluent yielded eudistidine C (3, 3.2 mg, 0.34%).

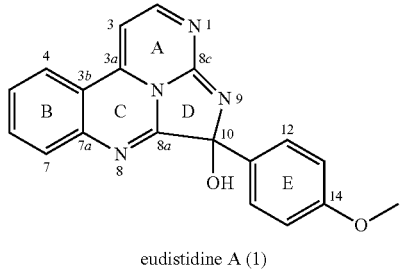

eudistidine A (1)

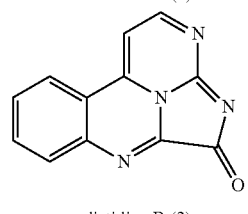

eudistidine B (2)

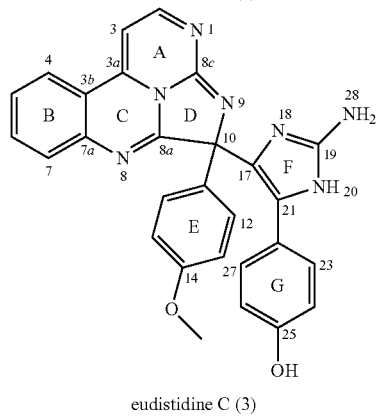

eudistidine C (3)

Eudistidine A (1) was isolated as an optically inactive compound (no optical rotation $[\alpha]_D$ or absorptions in the CD spectrum when recorded in DMSO) with a molecular formula of $C_{19}H_{14}N_4O_2$ that was established by HRESI mass spectrometry and required fifteen degrees of unsaturation. Eudistidine A (1): green oil; UV (DMSO) $\lambda_{max}$ (log ε) 327 (2.51), 450 (2.53); IR $\lambda_{max}$ 1945, 1612, 1353, 1249, 1026; $^1$H and $^{13}$C NMR data are shown in Table 2; (+)HRESIMS m/z 331.1184 [M+H]$^+$ (calculated for $C_{19}H_{15}N_4O_2$, 331.1190). The lack of optical activity indicated that the natural product apparently consists of a mixture of epimers at C-10.

The highly aromatic character of 1 was apparent from the presence of seventeen sp$^2$ carbons and only two sp$^3$ carbon signals ($\delta_C$ 55.1 and 94.4) in the $^{13}$C NMR spectrum (Table 2). Resonances attributable to 10 aromatic protons ($\delta_H$ 8.54, 8.40, 7.92, 7.85, 7.71, 7.54, 6.95, 6.91), one methoxyl ($\delta_H$ 3.74, 3H) and one hydroxyl group ($\delta_H$ 6.86) were observed in the $^1$H NMR spectrum (DMSO-d$_6$). COSY NMR data identified the presence of three proton-proton spin-systems: a 1,2-disubstituted benzene ring [$\delta_H$ 8.40 (d, J=8.2 Hz), 7.92 (dt, J=1.1, 7.6 Hz), 7.85 (d, J=8.0 Hz), 7.71 (dt, J=1.0, 7.6 Hz)], a para-substituted benzene ring [($\delta_H$ 7.54, 2H (d, J=8.8 Hz), 6.91, 2H (d, J=8.9 Hz)], and two mutually-coupled heteroaromatic protons [($\delta_H$ 8.54 (d, J=4.9 Hz), 6.95 (d, J=4.8 Hz)]. HSQC and HMBC data confirmed both the 1,2-disubstituted ring (designated as ring B) and the para-substituted benzene ring (ring E), and established the presence of a methoxyl group on the latter ring.

Deshielded carbon and proton chemical shifts ($\delta_C$ 166.2/ 6n 8.54) observed for the C-2 aromatic methine indicated it was situated directly adjacent to a nitrogen, while the highly shielded signals for C-3 ($\delta_C$ 92.2/$\delta_H$ 6.95) suggested the presence of additional nitrogen functionality in ring A. The position of C-3a in the A ring and its linkage to ring B were revealed by HMBC correlations from H-2, H-3, and H-4. An HMBC correlation from H-3 to C-3b confirmed the A-B ring linkage, while the deshielded chemical shift of C-3a ($\delta_C$ 144.5) indicated it was directly bound to a nitrogen atom. An HMBC correlation from H-2 to a quaternary carbon resonance at $\delta_C$ 154.8 (C-8c) suggested this carbon was part of a conjugated guanidino moiety. This functionality could be accommodated by linking C-8c with the nitrogen (N-8b) that was also joined to C-3a, to give a pyrimidine core for ring A. Observed correlations in the HMBC spectrum from protons at $\delta_H$ 8.40 (H-4) and 7.92 (H-6) to a deshielded carbon resonance $\delta_C$ 145.7 (C-7a), and from $\delta_H$ 7.85 (H-7) and 7.71 (H-5) to $\delta_C$ 117.0 (C-3b) suggested that ring B was fused with another nitrogen-containing heterocycle (ring C). A weak 4-bond HMBC correlation from H-3 in ring A to a carbon resonance at $\delta_C$ 160.0 was also observed. The deshielded nature of this aromatic carbon suggested it was directly bound to more than one nitrogen atom, and the fact that no other HMBC correlations were observed indicated that it was remote from all other aromatic protons. This carbon (C-8a) was assigned to a second fused pyrimidine ring (ring C) that incorporated nitrogens N-8 and N-8b, and was situated between rings A and B. $^1$H-$^{15}$N HMBC correlations from H-2 and H-3 to N-1 ($\delta_N$ 255.9), H-3 to N-8b ($\delta_N$ 164.0), and H-7 to N-8 ($\delta_N$ 254.2) supported both this assignment and the fused nature of rings A, B, and C.

HMBC correlations observed from the methoxyl protons ($\delta_H$ 3.74) to a carbon resonance at $\delta_C$ 159.1 (C-14), as well as from the aromatic protons at $\delta_H$ 7.54 (H-12/H-16) to C-14 and from $\delta_H$ 6.91 (H-13/H-15) to both $\delta_C$ 133.4 (C-11) and 113.3 (C-13/C-15), defined the para-methoxy-substituted benzene ring (E). A correlation from the H-12/H-16 protons to a quaternary carbon resonance at $\delta_C$ 94.4 revealed this carbon (C-10) was the connection point between ring E and the rest of the molecule. The chemical shift of C-10 was appropriate for a hemiaminal functionality, and this was supported by an HMBC correlation from the hydroxyl proton at $\delta_H$ 6.86 to C-10. An HMBC correlation from the OH proton to C-8a ($\delta_C$ 160.0) also revealed that C-8a and C-10 were adjacent. One additional ring was needed to satisfy the unsaturation equivalents implicit in the molecular formula of 1. This was accommodated by linking together C-10 and N-9 to form an imidazole ring (D), which then completed the planar structural assembly of eudistidine A (1). The pentacyclic framework of eudistidine A (1) contains several novel structural elements. Specifically, the 4-hydroxy, 4-aryl, 5-imino dihydroimidazole ring system and the fused pyrimido-quinazoline heterocycle are unprecedented in the natural product literature. These rare structural features are suggestive of an unusual biogenesis of 1.

While a ring-opened tautomeric structure of 1 (structure (b) below) can be envisioned, the presence of both a sharp hydroxyl proton signal ($\delta_H$ 6.86) and a hemiaminal carbon resonance ($\delta_C$ 94.4), and the lack of any signal for a ketone carbon in either the $^{13}$C NMR spectrum or the IR spectrum of 1, indicated that the cyclized form (structure (a) below) is predominant under all conditions examined to date.

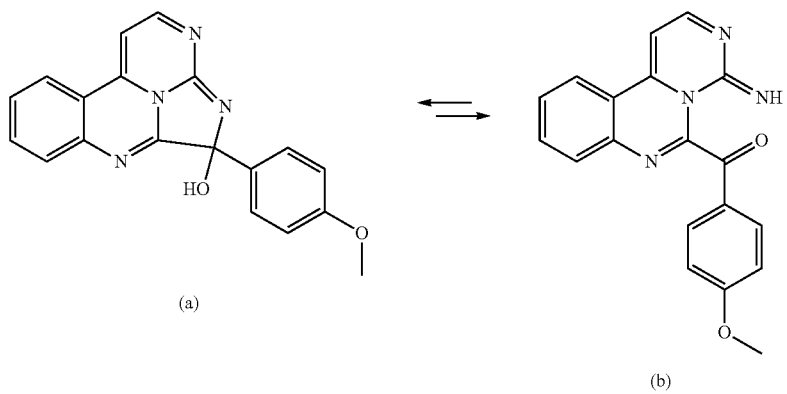 [SMILES: COc1ccc(C2(O)N=C3N=CC=C4c5ccccc5N=C2N43)cc1 ; COc1ccc(C(=O)c2nc3ccccc3c3ccnc(=N)n23)cc1]

(a)

(b)

TABLE 2

NMR spectroscopic data for eudistidine A (1) in DMSO-$d_6$

| position | $\delta_C$ | $\delta_N{}^a$ | $\delta_H$ (mult, J in Hz) | HMBC |
|---|---|---|---|---|
| 1 | | 255.9 | | |
| 2 | 166.2 | | 8.54 (d, 4.9) | 3, 3a, 3b, 8c |
| 3 | 92.2 | | 6.95 (d, 4.8) | 2, 3a, 3b, 8a$^c$ |
| 3a | 144.5 | | — | — |
| 3b | 117.0 | | — | — |
| 4 | 125.5 | | 8.40 (d, 8.2) | 3a, 6, 7a |
| 5 | 128.7 | | 7.71 (dt, 1.0, 7.6) | 3b, 7 |
| 6 | 135.0 | | 7.92 (dt, 1.1, 7.6) | 4, 7a |
| 7 | 128.6 | | 7.85 (d, 8.0) | 3b, 5 |
| 7a | 145.7 | | — | — |
| 8 | | 254.2 | | |
| 8a | 160.0 | | — | — |
| 8b | | 164.0 | | |
| 8c | 154.8 | | — | — |
| 9 | | n.o.$^b$ | | |
| 10 | 94.4 | | — | — |
| 10-OH | — | | 6.86 (s) | 8a, 10, 11 |
| 11 | 133.4 | | — | — |
| 12/16 | 127.5 | | 7.54 (d, 8.8) | 10, 11, 12/16, 14 |
| 13/15 | 113.3 | | 6.91 (d, 8.9) | 13/15, 14 |
| 14 | 159.1 | | — | — |
| 14-OMe | 55.1 | | 3.74 (s) | 14 |

$^a$$^{15}$N assignments were based on $^1$H-$^{15}$N HMBC correlations. The $\delta_N$ values were not calibrated to an external standard but were referenced to neat NH$_3$ (δ0.00) using the standard Bruker parameters.
$^b$not observed.
$^c$weak four-bond HMBC correlation.

Figure 3:
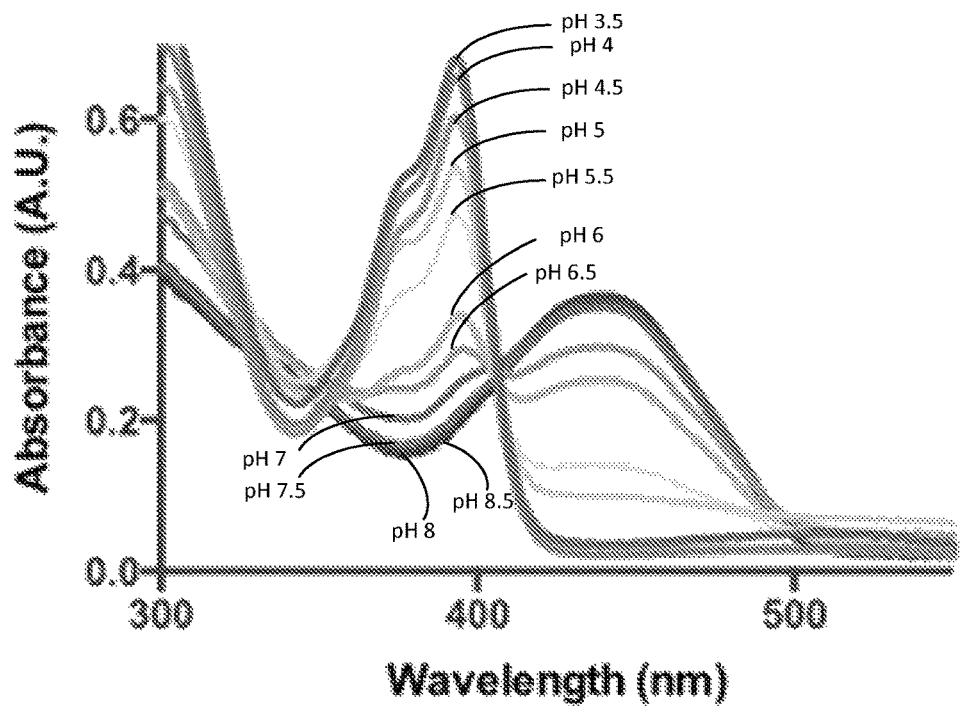
FIG. 3 shows pH effects on the UV absorption spectra of eudistidine A (1).

The extended pi-conjugation of eudistidine A (1) prompted an evaluation of its UV absorption properties. While only sparingly soluble in methanol, 1 showed excellent solubility in DMSO and good aqueous solubility. UV absorption maxima in DMSO were observed at 327 and 450 nm (FIG. 3). In aqueous solutions the absorption profile was strongly pH dependent. Local absorption maxima were observed at 393 nm and 440 nm in acidic and basic conditions, respectively, and an isosbestic point at 407 nm. The p$K_a$ of the titratable proton in 1 was 5.1±0.1

Eudistidine B (2) was isolated as a yellow-green oil and its molecular formula of $C_{12}H_6N_4O$ was established by (+)-HRESI mass spectrometry. The molecular formula was indicative of an aromatic heterocyclic structure and it required the presence of 12 unsaturation equivalents. Eudistidine B (2): yellow-green oil; UV (DMSO) $\lambda_{max}$ (log ε) 327 (3.07), 445 (2.68); IR $\lambda_{max}$ 1596, 1396, 1026; $^1$H and $^{13}$C NMR data are shown in Table 3; (+)HRESIMS m/z 223.0613 [M+H]$^+$ (calculated for $C_{12}H_7N_4O$, 223.0614).

TABLE 3

NMR spectroscopic data for eudistidine B (2) in DMSO-$d_6$

| position | $\delta_C$ | $\delta_H$ (mult, J in Hz) | HMBC |
|---|---|---|---|
| 2 | 163.8 | 9.10 (d, 5.6) | 3, 3a, 8c |
| 3 | 102.2 | 8.26 (d, 5.8) | 3, 3a, 3b |
| 3a | 144.2 | — | — |
| 3b | 117.3 | — | — |
| 4 | 126.5 | 9.00 (d, 7.9) | 3a, 6, 7a |
| 5 | 131.6 | 8.16 (t, 7.6) | 3b, 7 |
| 6 | 136.6 | 8.33 (t, 7.6) | 4, 7a |
| 7 | 130.9 | 8.44 (d, 8.1) | 3b, 5 |
| 7a | 145.6 | — | — |
| 8a | 142.5 | — | — |
| 8c | 163.3 | — | — |
| 10 | 172.0 | — | — |

Direct comparison of the NMR data for 2 (Table 3) with those obtained for eudistidine A (1) revealed that the hydroxyl moiety and the para-substituted benzene ring in 1 were not present in 2. However, analysis of the $^1$H, $^{13}$C, COSY, HSQC, and HMBC NMR data confirmed that the same fused ring system substructure observed in compound 1 (rings A, B, and C) was also present in 2. There was a consistent downfield shift for all of the protons present in eudistidine B (2), while the carbon resonances for C-3, C-8c and C-10 were shifted downfield relative to those in 1, while C-8a was shifted upfield. The most significant change was the absence of the C-10 hemiaminal carbon resonance at $\delta_C$ 94.4 and the appearance of a resonance at $\delta_C$ 172.0. This revealed the presence of an amide carbonyl functionality that was bound to nitrogen N-9, and it allowed assignment of the structure of eudistidine B (2).

Figure 4:
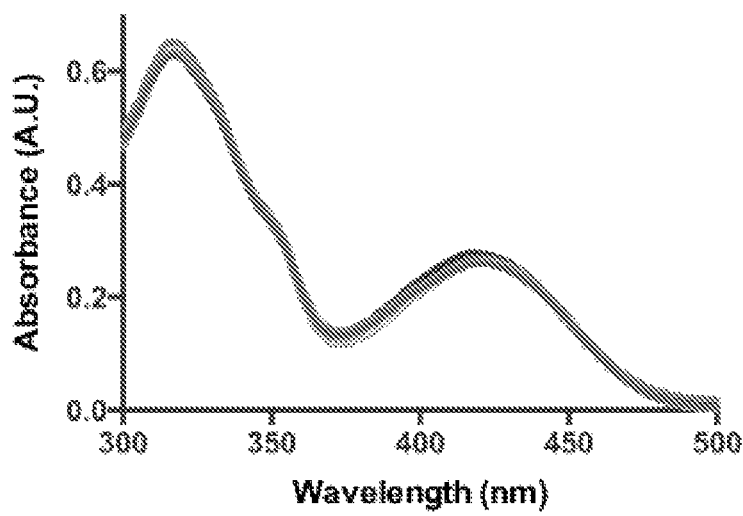
FIG. 4 shows pH effects on the UV absorption spectra of eudistidine B (2).

Eudistidine B (2) had rather poor solubility in MeOH so DMSO was used for the UV studies, which showed $\lambda_{max}$ at 327 and 445 nm (FIG. 4). In contrast to eudistidine A (1), compound 2 showed no pH dependence in its UV absorption profile over a pH range of 3-11, with similar absorption maxima in DMSO and water (327 nm and 445 nm in DMSO; 317 nm and 420 nm in H$_2$O).

Eudistidine C (3) was isolated as an optically inactive yellow oil with a molecular formula of $C_{28}H_{21}N_7O_2$, that required 22 degrees of unsaturation. The presence of the tetracyclic core (rings A-D), and the methoxyl containing para-substituted benzene ring (ring E) were confirmed by direct comparison of NMR data for eudistidine C with those for eudistidines A (1) and B (2). In addition, HSQC and HMBC data identified the presence of a second para-substituted benzene ring (ring F). The chemical shift for C-10 ($\delta_C$ 73.7) suggested that C-10 of eudistidine C was not a hemiaminal functionality. The structure of the remaining fragment of $C_3N_3H_3$ could not be fully identified using conventional NMR analyses. An observed HMBC correlation from H-23/27 ($\delta_H$ 6.85) of ring G to a carbon chemical shift at $\delta_C$ 127.5 (one of the three quaternary carbons of this fragment) indicated the unknown fragment was connected to ring G. A carbon chemical shift at $\delta_C$148.0 suggested the presence of a guanidine functionality. Therefore, the $C_3N_3H_3$ fragment was proposed to be an amino-imidazole ring (ring F). None of the exchangeable NH protons were observed in DMSO-$d_6$ or CD$_3$OH and eudistidine C was somewhat unstable in DMSO-$d_6$. The NMR data were analyzed by the ACD Structure Elucidator program and the proposed structure was ranked the most probable result. In addition, crucial $^4J_{CH}$ and $^5J_{CH}$ correlations observed in the 2 Hz optimized LR-HSQMBC$^5$ experiment from H-12/16 (ring E) to C-8a and C-17 (ring F), as well as from H-23/27 (ring G) and H-24/26 (ring G) to C-17 (ring F) further confirmed the proposed planar structure of eudistidine C (3). $^1$H and $^{13}$C NMR data for eudistidine C (3) are shown in Table 4.

TABLE 4

NMR spectroscopic data for eudistidine C (3) in CD$_3$OD-$d_4$

| position | $\delta_C$ | $\delta_H$ (mult, J in Hz) | HMBC |
|---|---|---|---|
| 2 | 167.5 | 8.45 (d, 5.0) | 3, 3a, 3b, 8c |
| 3 | 94.3 | 6.77 (d, 5.3) | 2, 3a, 3b |
| 3a | 147.4 | — | — |
| 3b | 117.6 | — | — |
| 4 | 126.1 | 8.06 (d, 8.0) | 3a, 6, 7a |
| 5 | 130.2 | 7.58 (t, 7.5) | 3b, 7 |
| 6 | 136.5 | 7.81 (t, 7.5) | 4, 7a |
| 7 | 129.7 | 7.65 (d, 8.0) | 3b, 5 |
| 7a | 147.0 | — | — |
| 8a | 159.5 | — | — |
| 8c | 157.3 | — | — |

TABLE 4-continued

NMR spectroscopic data for eudistidine C (3) in CD$_3$OD-d$_4$

| position | $\delta_C$ | $\delta_H$ (mult, J in Hz) | HMBC |
|---|---|---|---|
| 10 | 73.7 | — | — |
| 11 | 130.9 | — | — |
| 12/16 | 129.8 | 7.68 (d, 8.9) | 10, 12/16, 14 |
| 13/15 | 115.2 | 6.91 (d, 8.8) | 11, 13/15, 14 |
| 14 | 161.7 | — | — |
| 14-OMe | 55.8 | 3.76 (s) | 14 |
| 17 | 126.1 | — | — |
| 19 | 148.0 | — | — |
| 21 | 127.5 | — | — |
| 22 | 120.0 | — | — |
| 23/27 | 131.9 | 6.85 (d, 8.8) | 21, 23/27, 25 |
| 24/26 | 115.7 | 6.30 (d, 8.5) | 22, 24/26, 25 |
| 25 | 159.3 | — | — |

Example 3

Synthesis of Naturally Occurring Eudistidines and Analysis

While the structures of eudistidine A (1) and eudistidine B (2) were assigned based on a comprehensive analysis and interpretation of their NMR spectroscopic data, the proton-deficient and heteroatom-rich nature of rings A, C, and D made definitive proof of their structures difficult. Given the unprecedented constellation of rings and heteroatoms in the eudistidines, spectral comparisons with known compounds were of limited value. A total synthesis of compounds 1 and 2 would serve to both confirm the assigned structures and provide sufficient quantities of these compounds to support more detailed biological and biochemical evaluations. The general retrosynthetic approach is outlined in Scheme 1 (FIG. 1). The tautomeric structure in which the D ring is opened could feasibly be a minor component of 1, and it was a readily apparent synthetic precursor to eudistidine A. It was envisaged that this tautomer could be formed from 4-(2-aminophenyl)pyrimidin-2-amine (4) and 4-methoxyphenylglyoxal (5) through a sequential condensation, cyclization, and oxidation reaction process. A related sequence with 3 and glyoxylic acid (6) was also anticipated to provide 2.

In brief, the synthesis of 1 was accomplished as follows (FIG. 2). The key precursor, 4-(2-aminophenyl)pyrimidin-2-amine (4), was synthesized in three steps from 1-(2-nitrophenyl)ethanone as reported previously (Agarwal et al., Tetrahedon 2009, 65:1153-1161), but with a slight modification at the last step. By using Pd/C to hydrogenate 4-(2-nitrophenyl)pyrimidin-2-amine, instead of HCl and iron as described in the literature, compound 4 could readily be prepared on a multi-gram scale. Intermediate 4, which provided rings A and B and all four nitrogen atoms in 1, was used in the subsequent step without further purification after verification of its structure by LCMS and $^1$H NMR. The aryl glyoxal reagent 5 was generated via a Kornblum oxidation of 2-bromo-4'-methoxyacetophenone in DMSO/water and was used immediately without further purification (WO 2004/085408 A1). Efficient condensation of reagents 4 and 5, followed by oxidative conversion to eudistidine A (1) was ultimately accomplished through a one-pot sequence consisting of dropwise addition of in situ generated aryl glyoxal 5 to a DMSO solution of 4, mild heating (1 h, 65° C.) presumably to promote condensation and cyclization, and then finally in situ oxidation with one equivalent of I2 (1 h, 65° C.). Purification of the reaction product by reversed-phase C$_{18}$ HPLC provided compound 1 in excellent yield (70%), which was identical by MS and NMR with the natural product eudistidine A. Significant optimization was required to develop the conditions used in the final key step. For example, precondensation of the aryl glyoxal 5 with intermediate 4 was required, as the simultaneous addition of 5 and iodine to 4 provided 1 in only trace quantities. Moreover, evaluation of a series of different oxidants [I$_2$, DDQ, MnO$_2$, Fe(III)] in the reaction sequence revealed that iodine alone provided both a high yield of 1 and the most reliable results.

Using a similar strategy, eudistidine B (2) was synthesized by heating a solution of glyoxylic acid (6) and 4-(2-aminophenyl)pyrimidin-2-amine (4) at 60° C. for 18 hours in DMF to provide the desired product 2 in 36% yield. In this instance, the inclusion of exogenous oxidants was not beneficial. Without wishing to be bound by a particular theory of operation, it is likely that ambient O$_2$ was involved in the process. The spectroscopic data for the synthetic material were in complete agreement (MS, $^1$H NMR and $^{13}$C NMR) with those obtained with the natural product, eudistidine B (2).

The syntheses of eudistidines A (1) and B (2) were both accomplished in a concise, scalable, and economic manner with quite acceptable overall yields. These efforts help to confirm the assigned structures of the natural products and opened the way for large-scale production and analogue development.

Synthesis of (E)-3-dimethylamino-1-(2-nitrophenyl) prop-2-en-1-one

A solution of 1-(2-nitrophenyl)ethanone (4 g, 24.22 mmol) and 1,1-dimethoxy-N,N-dimethylmethanamine (3.22 ml, 24.22 mmol) was heated neat to 105° C. for 3 h. The mixture was taken up in CH$_2$Cl$_2$ and then purified by SiO$_2$ chromatography (100 G, 50-100% EtOAc-hexanes) to give the desired product.

Synthesis of 4-(2-nitrophenyl)pyrimidin-2-amine

A mixture of (E)-3-(dimethylamino)-1-(2-nitrophenyl) prop-2-en-1-one (1.1 g, 4.99 mmol), potassium carbonate (2.416 g, 17.48 mmol), and guanidine hydrochloride (1.432 g, 14.98 mmol) in EtOH (20 ml) was heated to reflux overnight. The mixture was then cooled to room temperature and concentrated. The residue was taken up in EtOAc and water, and extracted repeatedly with EtOAc. The combined EtOAc solutions were dried, filtered, and concentrated to give a yellow solid that was used without further purification.

Synthesis of 4-(2-aminophenyl)pyrimidin-2-amine (4)

A solution of 4-(2-nitrophenyl)pyrimidin-2-amine (200 mg, 0.925 mmol) in a mixture of 1:1 EtOH-EtOAc (40 mL) was treated with Pd/C (40 mg), purged with hydrogen, and allowed to stir overnight. The suspension was filtered through a pad of Celite, and the filtrate was evaporated and dried in vacuo. The product, 4-(2-aminophenyl)pyrimidin-2-amine (152.0 mg, 88%), was used in the next step without further purification.

Synthesis of eudistidine A (1)

A solution of 2-bromo-4'-methoxyacetophenone (50 mg, 0.22 mmol) in DMSO (0.30 mL) and water (0.01 mL) was heated at 65° C. for 3 hours to generate 2-(4-methoxyphenyl)-2-oxoacetaldehyde (5). The solution was cooled to room temperature, diluted with additional DMSO (0.42 mL) and added dropwise to a stirring solution of 4-(2-aminophenyl)pyrimidin-2-amine (4), 30 mg, 0.16 mmol) in DMSO (0.54 mL) at 0° C. The resulting reaction mixture was then heated at 60° C. for 30 mins, followed by addition of I2 (41 mg, 0.16 mmol) and continued heating at 60° C. for an additional 1 hr. The reaction solution was then injected directly onto a reversed-phase preparative $C_{18}$ HPLC column, employing a gradient of 20-60% MeCN—$H_2O$ (1% $NH_4OH$) over 10 mins to yield eudistidine A (1, 37.0 mg, 70%). IR (thin film) $\lambda_{max}$ 3045, 1646, 1625, 1501, 1349, 1245, 1166 cm$^{-1}$; $^1H$ NMR (DMSO-$d_6$, 600 MHz) δ 8.54 (1H, d, J=4.9 Hz, H-2), 8.41 (1H, dd, J=8.1, 1.0 Hz, H-4), 7.92 (1H, td, J=7.7, 1.1 Hz, H-6), 7.85 (1H, d, J=7.7 Hz, H-7), 7.71 (1H, td, J=7.7, 1.1 Hz, H-5), 7.54 (2H, d, J=8.8 Hz, H-12/16), 6.94 (1H, d, J=4.8 Hz, H-3), 6.91 (2H, d, J=8.8 Hz, H-13/15), 6.86 (1H, br s, H-10OH), 3.74 (3H, s, H-14OCH$_3$); $^{13}C$ NMR (DMSO-$d_6$, 150 MHz) δ 166.1 (C-2), 159.9 (C-8a), 159.0 (C-14), 154.7 (C-8c), 145.6 (C-7a), 144.4 (C-3a), 134.8 (C-6), 133.3 (C-11), 128.6 (C-5), 128.5 (C-7), 127.4 (C-12/16), 125.4 (C-4), 116.9 (C-3b), 113.2 (C-13/15), 94.3 (C-10), 92.0 (C-3), 55.0 (C-14OCH$_3$); (+)HRESIMS m/z 331.1190 [M+H]$^+$ (calculated for $C_{19}H_{15}N_4O_2$, 331.1190).

Synthesis of eudistidine B (2)

A solution of 4-(2-aminophenyl)pyrimidin-2-amine (4, 20 mg, 0.12 mmol) in DMF (12 mL) was treated with glyoxylic acid monohydrate (6, 44 mg, 0.6 mmol) and allowed to heat at 60° C. overnight. Purification by reversed-phase $C_{18}$ flash chromatography eluting with 0-25% MeOH—$H_2O$ gave eudistidine B (2, 10.1 mg, 38%). IR (thin film) $\lambda_{max}$ 1697, 1600, 1487, 1438, 1245, 1166 cm$^{-1}$; $^1H$ NMR (DMSO-$d_6$, 600 MHz) δ 9.09 (1H, d, J=5.7 Hz, H-2), 8.99 (1H, d, J=8.0 Hz, H-4), 8.44 (1H, d, J=8.0 Hz, H-7), 8.32 (1H, t, J=7.8 Hz, H-6), 8.26 (1H, d, J=5.6 Hz, H-3), 8.16 (1H, t, J=7.6 Hz, H-5); $^{13}C$ NMR (DMSO-$d_6$, 150 MHz) δ 172.0 (C-10), 163.8 (C-2), 163.3 (C-8c), 145.6 (C-7a), 144.2 (C-3a), 142.5 (C-8a), 136.6 (C-6), 131.7 (C-5), 130.9 (C-7), 126.5 (C-4), 117.3 (C-3b), 102.2 (C-3); (+)HRESIMS m/z 223.0613 [M+H]$^+$ (calculated for $C_{12}H_7N_4O$, 223.0614).

Synthesis of Eudistidine C (3)

A solution of eudistidine A (1) in DMSO-5% aqueous trifluoroacetic acid was stirred with 1.5 equivalents of 4-(2-amino-1H-imidazol-5-yl)phenol for 36 hours at 25° C. to give eudistidine C (3). NMR data for natural eudistidine C, synthetic eudistidine C, and the TFA salt of synthetic eudistidine C is shown in Table 5.

TABLE 5

NMR data of natural eudistidine C, synthetic eudistidine C, and the TFA salt of synthetic eudistidine C.

| position | Natural Product $\delta_C$ (ppm) | Synthetic Free Base | Synthetic TFA salt |
|---|---|---|---|
| 2 | 167.5 | 167.5 | 167.4 |
| 3 | 94.3 | 94.4 | 101.8 |
| 3a | 147.4 | 147.5 | 147.8 |
| 3b | 117.6 | 117.8 | 117.6 |
| 4 | 126.1 | 126.2 | 127.2 |
| 5 | 130.2 | 130.2 | 132.0 |
| 6 | 136.5 | 136.5 | 138.4 |

TABLE 5-continued

NMR data of natural eudistidine C, synthetic eudistidine C, and the TFA salt of synthetic eudistidine C.

| position | Natural Product $\delta_C$ (ppm) | Synthetic Free Base | Synthetic TFA salt |
|---|---|---|---|
| 7 | 129.7 | 129.8 | 130.7 |
| 7a | 147.0 | 147.1 | 146.7 |
| 8a | 159.5 | 159.5 | 153.6? |
| 8c | 157.3 | 157.4 | 155.0 |
| 10 | 73.7 | 73.7 | 69.6 (hmbc) |
| 11 | 130.9 | 130.8 | 127.7 |
| 12/16 | 129.8 | 129.8 | 129.7 |
| 13/15 | 115.2 | 115.2 | 115.6 |
| 14 | 161.7 | 161.7 | 162.4 |
| 14-OMe | 55.8 | 55.8 | 55.6 |
| 17 | 126.1 | 125.8? | 122.7? |
| 19 | 148.0 | 148.1 | 148.4? |
| 21 | 127.5 | 127.5 | 129.0 |
| 22 | 120.0 | 119.9 | 118.4 |
| 23/27 | 131.9 | 131.9 | 132.1 |
| 24/26 | 115.7 | 115.7 | 115.6 |
| 25 | 159.3 | 159.3 | 159.9 |

UV-Vis Analysis.

100 μM solutions of 1 and 2 in 50 mM buffers at varied pH (citric acid; pKa=3.1, succinic acid; pKa=4.2, acetic acid; pKa=4.8, and phosphate) were prepared with a final DMSO concentration of 0.1%. The cuvettes were allowed to equilibrate for 1 h before a UV-Vis curve was obtained. The $pK_a$ for 1 was determined by fitting Δ abs at 394 and 440 nm to a polynomial curve, as described previously (Yapici et al., J. Am. Chem. Soc. 2015, 137:1073-1080).

Example 4

Synthesis of Eudistidine A Analogs

Three analogs of eudistidine A were made using a method similar to the synthesis of eudistidine A in Example 3, but with a different aryl glyoxal:

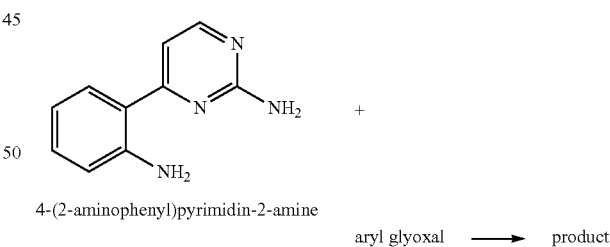

4-(2-aminophenyl)pyrimidin-2-amine aryl glyoxal ⟶ product

A mixture of bromoacetophenone in DMSO and water and heated at 65° C. for 3 hours. The solution was cooled to room temperature, diluted with additional DMSO and was added dropwise to a solution of 4-(2-aminophenyl)pyrimidin-2-amine in DMSO at 0° C. The resulting reaction mixture was heated at 60° C. for 30 mins followed by addition of I$_2$ and continued heating at 60° C. for 1 hr. The solution was injected directly onto a reversed-phase preparative HPLC, employing a gradient of 20-50% MeCN:H$_2$O (0.025% NH$_4$OH) over 10 mins to yield a phenyl analog EA-1. The yield was 44%.

EA-1

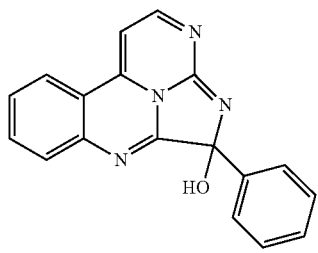

A mixture of 2-bromoacetylbenzoic acid in DMSO and water and heated at 65° C. for 3 hours. The solution was cooled to room temperature, diluted with additional DMSO and was added dropwise to a solution of 4-(2-aminophenyl) pyrimidin-2-amine in DMSO at 0° C. The resulting reaction mixture was heated at 60° C. for 30 mins followed by addition of I$_2$ and continued heating at 60° C. for 1 hr. The reaction was dried and size exclusion Sephadex LH20 eluting with MeOH was used to yield phenylbenzoic acid analog EA-2. The yield was 90%.

EA-2

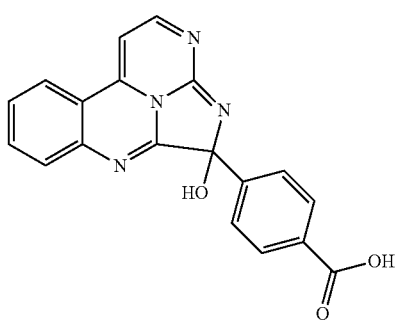

An alkyne-substituted analog EA-3 was made by reacting the phenylbenzoic acid analog with 1-amino-4-pentyne hydrochloride. The benzoic acid was treated with EDCI (1-ethyl-3-(3-dimethylaminopropyl)carbodiimide) and 4-pentyn-1-amine in dimethylformamide at room temperature. After 3 h the reaction was purified directly by reversed-phase preparative HPLC to yield the amide product. The yield was 40%.

EA-3

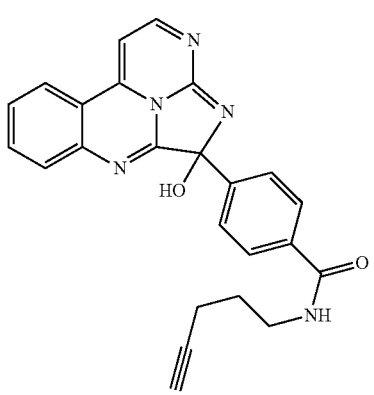

Seven additional analogs were synthesized by reacting eudistidine A with different nucleophiles.

Eudistidine A HBr salt (1 eq) was dissolved in DMSO and N-methyl indole (1.5 eq) was added. The solution was allowed to stand for 24 hr at room temperature. The solution was purified by reversed-phase preparative HPLC to yield the N-methyl indole analog EA-4. The yield was 83%.

EA-4

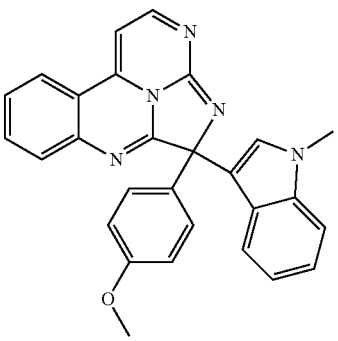

Eudistidine A HBr salt (1 eq) was dissolved in DMSO and skatole (10 eq) was added. The solution was allowed to stand for 7 days at 37° C. The solution was purified by reversed-phase preparative HPLC to yield the skatole analog EA-5. The yield was 35%.

EA-5

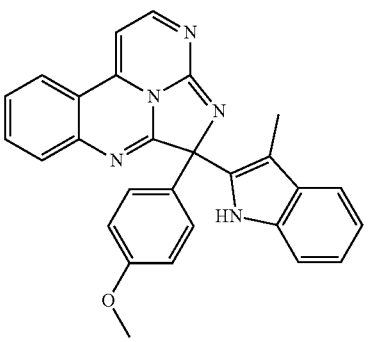

Eudistidine A HBr salt (1 eq) was dissolved in DMSO and phenol (39 eq) was added. The solution was allowed to stand for 6 days at 37° C. The solution was purified by reversed-phase preparative HPLC to yield the phenol analog EA-6. The yield was 27%.

EA-6

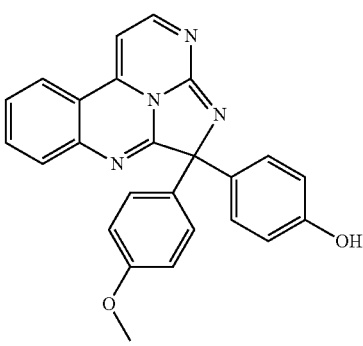

Eudistidine A HBr salt (1 eq) was dissolved in DMSO and resorcinol (11.5 eq) was added. The solution was allowed to stand for 24 hr at 37° C. The solution was purified by reversed-phase preparative HPLC to yield the resorcinol analog EA-7. The yield was 62%.

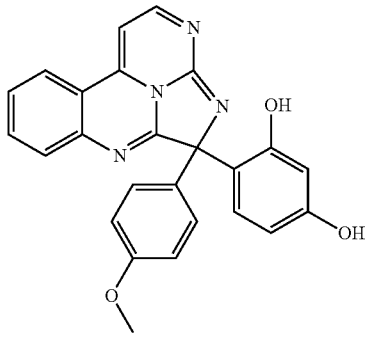

EA-7

Eudistidine A HBr salt (1 eq) was dissolved in DMSO and phloroglucinol (9.5 eq) was added. The solution was allowed to stand for 24 hr at room temperature. The solution was purified by reversed-phase preparative HPLC to yield the phloroglucinol analog EA-8. The yield was 55%.

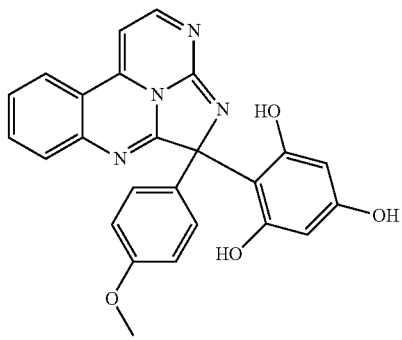

EA-8

Eudistidine A HBr salt (1 eq) was dissolved in DMSO and N-methyl pyrrole (1.5 eq) was added. The solution was allowed to stand for 24 hr at room temperature. The solution was purified by reversed-phase preparative HPLC to yield the N-methyl pyrrole analog EA-9. The yield was 71%. A trace amount of the bis-N-methyl pyrrole analog EA-10 was also obtained.

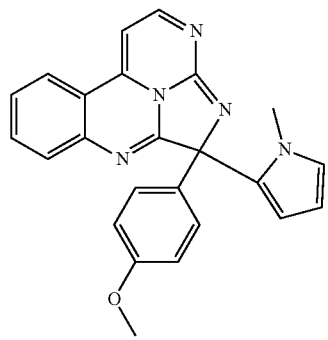

EA-9

-continued

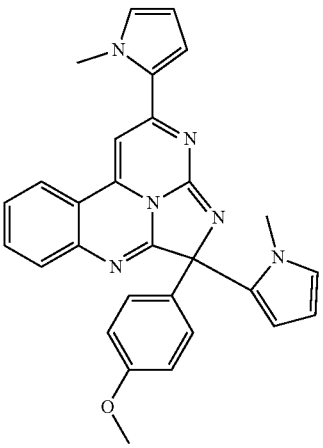

EA-10

Example 5

Inhibition of HIF-1α Binding to p300

Inhibition of HIF-1α binding to p300 was measured by displacement of GST-p300-CH1 (aa 323-423) from synthetic biotinylated HIF-1αC-TAD (aa 786-826; Peptide Protein Research Ltd., Fareham, UK) immobilized on 384-well streptavidin-coated plates. Bound GST-CH1 was detected using a europium-labeled antibody to GST (PerkinElmer Life Sciences). 48.5 nM HIF-1α C-TAD was used to coat plates for 5 h at room temperature. Plates were washed four times with TBST (50 mM Tris, 150 mM NaCl, 0.05% Tween 20, pH 8.0) buffer. 7.35 nM GST-CH1 was added along with the test compounds or control (1% DMSO) in TBST with 5% BSA, 0.5 mM DTT, and 10 μM $ZnCl_2$ and incubated overnight at 24° C. Plates were washed four times with TBST, and europium-labeled anti-GST (450 ng/mL) was added to plates in the same buffer used for GST-CH1 addition. After 2 h, plates were washed four times in TBST. DELFIA enhancement solution (PerkinElmer Life Sciences) was added and plates were placed on a rocker for 30 min, before reading with a Victor3 plate reader (PerkinElmer Life Sciences) or a Pherastar Plate Reader (BMG Labtech), using the europium setting under time-resolved fluorescence. Values were corrected for background and expressed as a percentage of controls (DMSO) to provide the percentage of CH1 binding.

Eudistidines A (1), B (2), and C (3), as well as analogs EA-1 and EA-2, were tested for their ability to inhibit the interaction of CH1 (p300) and C-TAD (HIF-1α) in a dose-response format of the screening assay. Naturally occurring eudistidine A (1) and eudistidine C (3) effectively blocked the binding of soluble CH1 to immobilized C-TAD with an $IC_{50}$ of approximately 75 μM, while eudistidine B (2) showed no inhibition at a high dose of 250 μM. Analog EA-1 showed no inhibition, even at high dose. Analog EA-2 had an $IC_{50}$ of approximately 100 μg/mL.

Figure 5A:
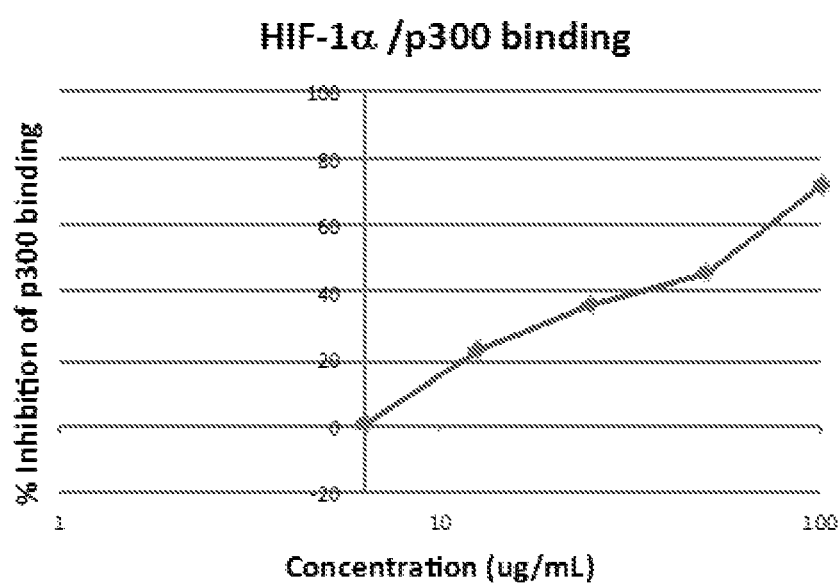
FIGS. 5A-5E are graphs of p300/HIF-1α binding assays with varying concentrations of natural eudistidine A, trifluoroacetic acid (TFA) salt (FIG. 5A), synthetic eudistidine A, TFA salt (FIG. 5B), natural eudistidine A, free base (FIG. 5C), natural eudistidine A, HCl salt (FIG. 5D), and natural eudistidine A, acetic acid salt (FIG. 5E).
Figure 5B:
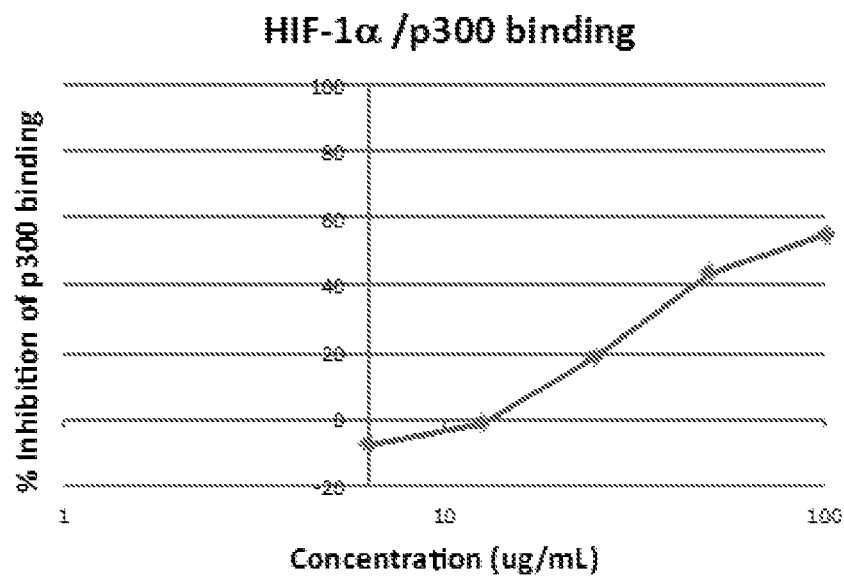
Figure 5C:
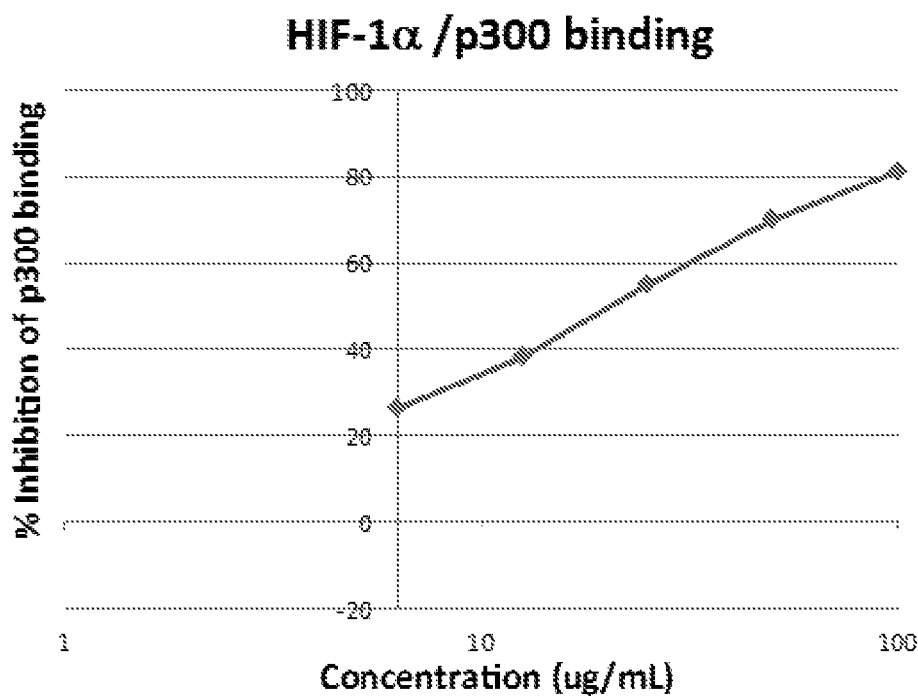
Figure 5D:
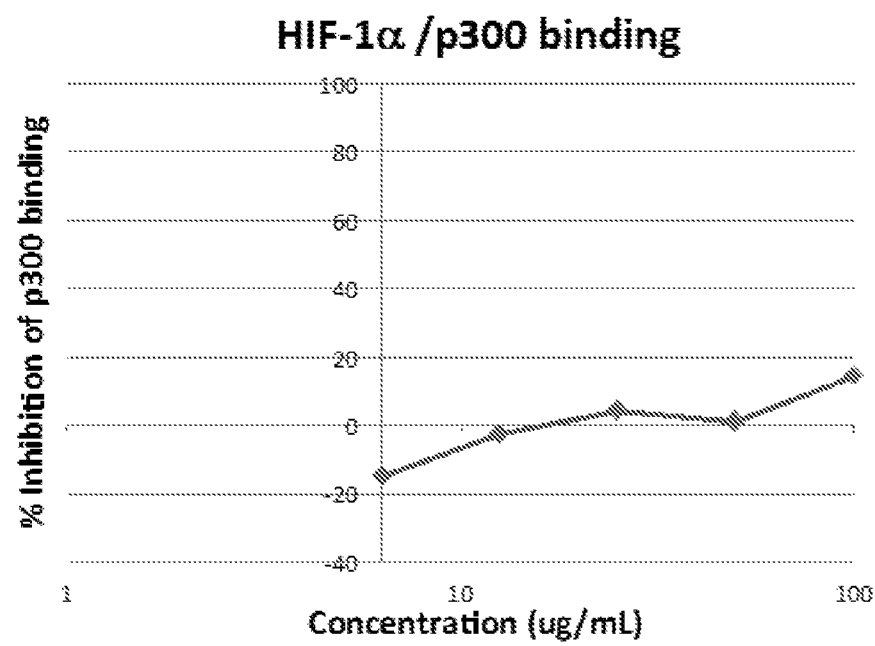
Figure 5E:
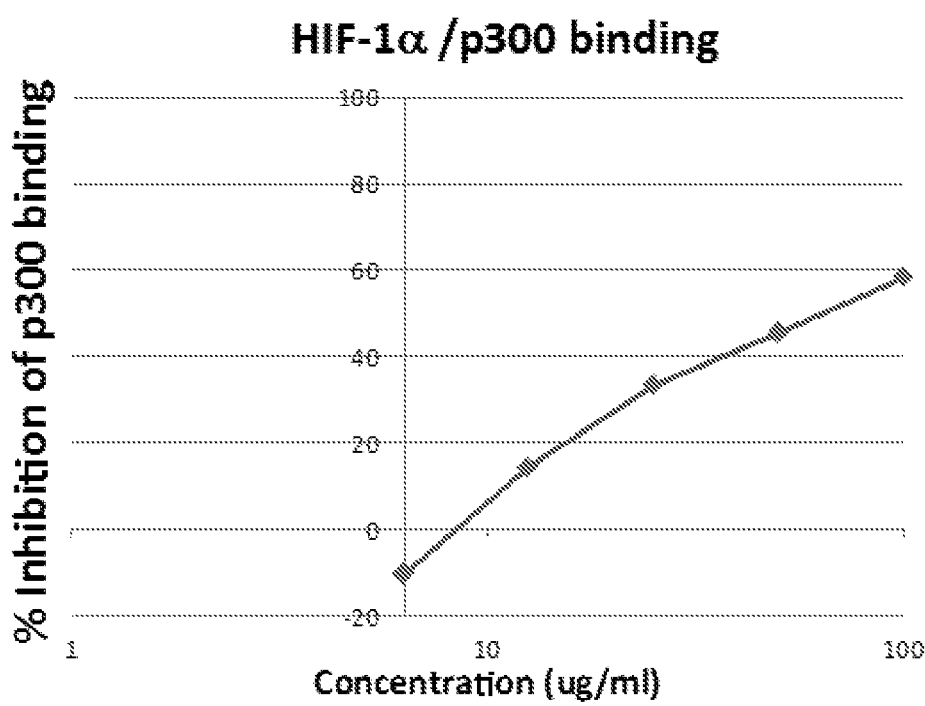

Eudistidine A (1) was initially isolated from the ascidian extract and characterized as its free base. Alkaloids are generally more stable as salts so several different salts were prepared by treatment of 1 with HCl, TFA, or acetic acid. FIGS. 5A-5E show that natural eudistidine A, TFA salt (FIG. 5A), synthetic eudistidine A, TFA salt (FIG. 5B), natural eudistidine A, free base (FIG. 5C), and natural eudistidine A, acetic acid salt (FIG. 5E) similarly inhibit HIF-1α binding to p300. FIG. 5D shows that the natural product, HCl salt, has greatly reduced activity compared to the TFA salt, free base, and acetic acid salt forms. Naturally occurring eudistidine A (1) effectively inhibited CH1/C-TAD binding with an $IC_{50}$ of 75 µM and synthetic 1 had similar activity.

Figure 6A:
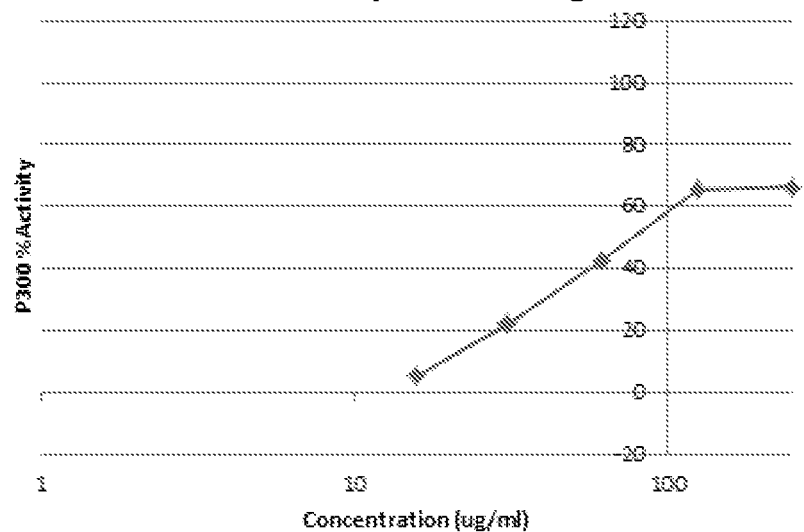
FIGS. 6A-6C are graphs showing three trials of a p300/HIF-1α binding assay with varying concentrations of synthetic eudistidine C, TFA salt.
Figure 6B:
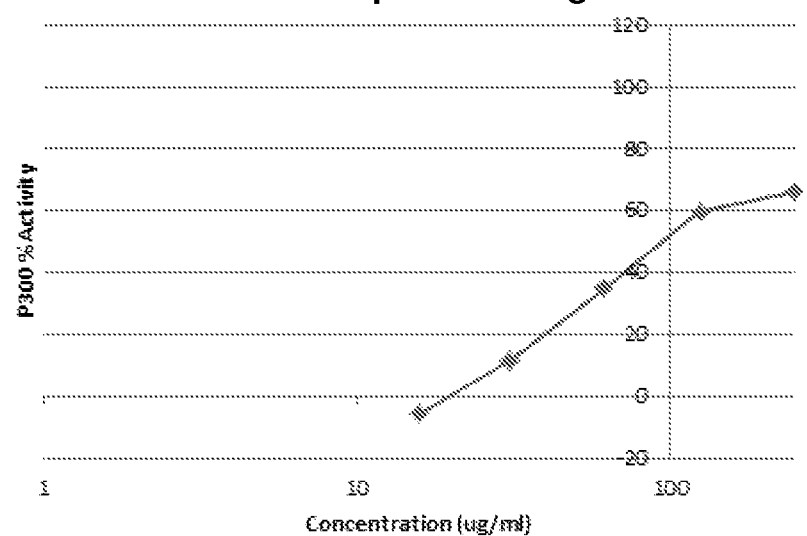
Figure 6C:
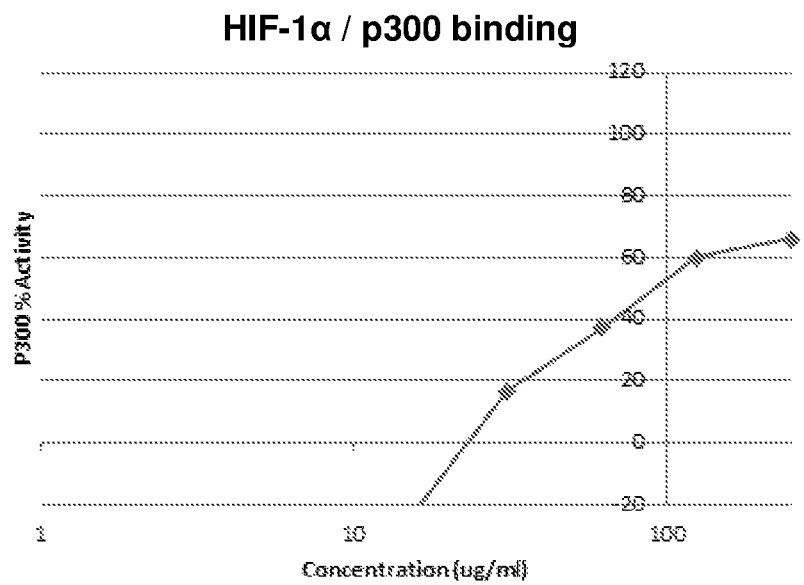

FIGS. 6A-6C are three trials showing the inhibitory effects of synthetic eudistidine C, TFA salt on binding of HIF-1α binding to p300. As shown in FIGS. 6A-6C, synthetic eudistidine C, TFA salt has an inhibitory activity very similar to that of synthetic eudistidine A, TFA salt (FIG. 5B).

In an effort to evaluate a broader range of potential activities of interest, compound 1 was screened against a commercial panel of 456 protein kinase enzymes and 32 bromodomain proteins (DiscoverRx, San Diego, Calif.), and it had no activity against any of these targets. These results suggest that the ability of 1 to inhibit the CH1/C-TAD interaction is not due to a non-specific propensity to bind to proteins, but is more specific for these two binding partners. Compound 1 was also tested at the standard initial concentration of 40 µM in the NCI-60 cell line anticancer screen, but it showed no significant cytotoxic activity.

Example 6

HIF-1α Blocking in HCT116 Cells Under Anoxic Conditions

Eudistidine A was shown to block HIF-1α activation in HCT116 cells under anoxic conditions. Activation was monitored via a hypoxia response element (HRE) luciferase signal. When HIF-1α is activated, it results in an increased HRE luciferase signal. If activation of HIF-1α is blocked due to inhibition of the p300/HIF-1α interaction, then the HRE luciferase signal is diminished.

Figure 7:
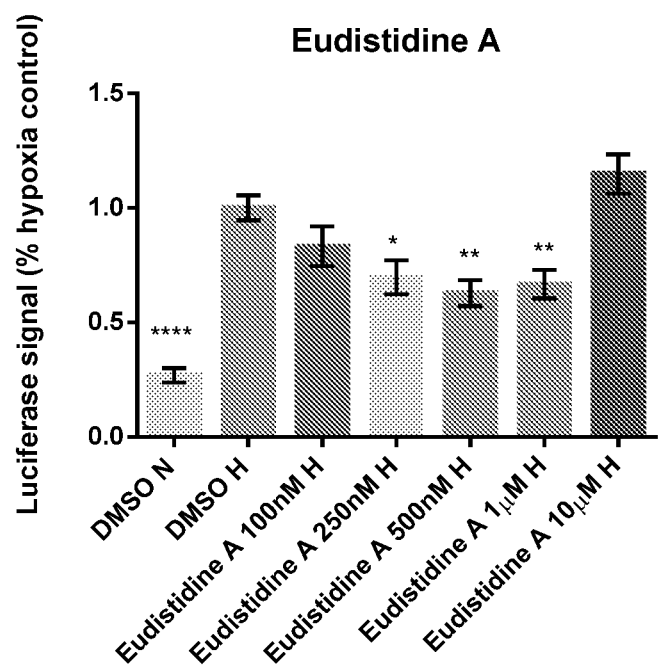
FIG. 7 is a graph showing effects of eudistidine A at various concentrations on HIF-1α activation in HCT116 cells under anoxic conditions.

The data in FIG. 7 is indicative of eudistidine A activity in a cellular setting except at the highest test concentration (10 µM), which may be an anomaly. Reporter activity values (ratio HRE:TK/average normoxia control) of eudistidine A are normalized to the hypoxia control and are expressed as the average of triplicate experiments ±S.E.M. (n-4). Data were analyzed using an ordinary one-way ANOVA with Dunnett's multiple comparisons test (reference group: DMSO.H). * P≤0.05,  P≤0.01, * P≤0.0001.

Figure 8:
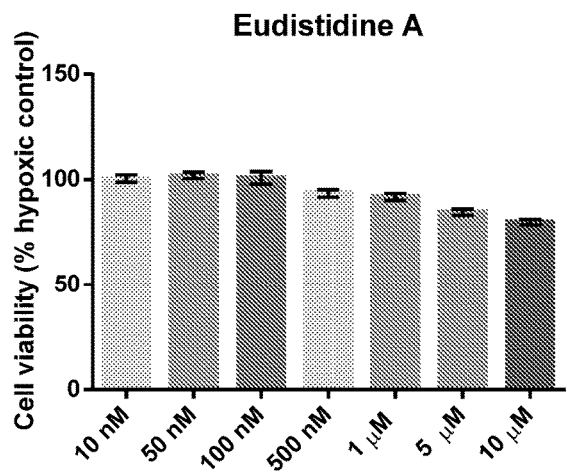
FIG. 8 is a graph showing CCK-8 cytotoxicity results for eudistidine A in HCT116 cells after 18 h treatment under hypoxic conditions (0.5% $O_2$).

FIG. 8 shows the results of CCK-8 cytotoxicity results for eudistidine A in HCT 116 cells are 18 h treatment under hypoxic conditions (0.5% $O_2$). Results are presented as the average cell viability number (% hypoxic control) of triplicate experiments ±S.E.M. (n=3-4). At the test concentrations eudistidine A had only modest cytotoxicity/growth inhibitory activity against this cell line.

Example 7

Antimalarial Activity

Eudistidine A and Eudistidine C were evaluated for antimalarial activity. The antimalarial activity was determined against chloroquine sensitive (D6) and chloroquine resistant (W2) strains of *P. falciparum* by measuring plasmodial LDH (lactate dehydrogenase) activity according to the procedure of Makler and Hinrichs (*Am. J. Trop. Med. Hyg.* 1993, 48:205). A suspension of red blood cells infected with D6 or W2 strain of *P. falciparum* (200 µL, with 2% parasitemia and 2% hematocrit in RPMI 1640 medium supplemented with 10% human serum and 60 µg/mL Amikacin) was added to the wells of a 96-well plate containing 10 µL of serially diluted samples (plant extracts, column fractions or pure compounds). The plate was incubated at 37° C., for 72 h in a modular incubation chamber with 90% $N_2$, 5% $O_2$, and 5% $CO_2$. Parasitic LDH activity was determined by mixing 20 µL of the incubation mixture with 100 µL of the Malstat reagent and incubating at room temperature for 30 min Twenty microliters of a 1:1 mixture of NBT/PES (nitro blue tetrazolium/phenazine ethosulfate) (Sigma, St. Louis, Mo.) was then added and the plate was further incubated in the dark for 1 h. The reaction was stopped by adding 100 µL of a 5% acetic acid solution and the absorbance was read at 650 nm. Artemisinin and chloroquine were included as the drug controls. $IC_{50}$ values were computed from the dose response curves of growth inhibition.

The in vitro cytotoxicity of samples to mammalian cells was also tested in order to determine the selectivity index of the antimalarial activity. The assay was performed in 96-well tissue culture-treated plates. Vero cells (monkey kidney fibroblasts) were seeded to the wells of 96-well plate at a density of 25,000 cells/well and grown for 24 h. Samples at different concentrations were added and cells were further incubated for 48 h. Cell viability was determined by Neutral Red method (Borenfreund et al., *In vitro Dev. Cell. Bol.* 1990, 26:1030). $IC_{50}$ values were obtained from dose response curves. Doxorubicin was included as drug control.

Figure 9:
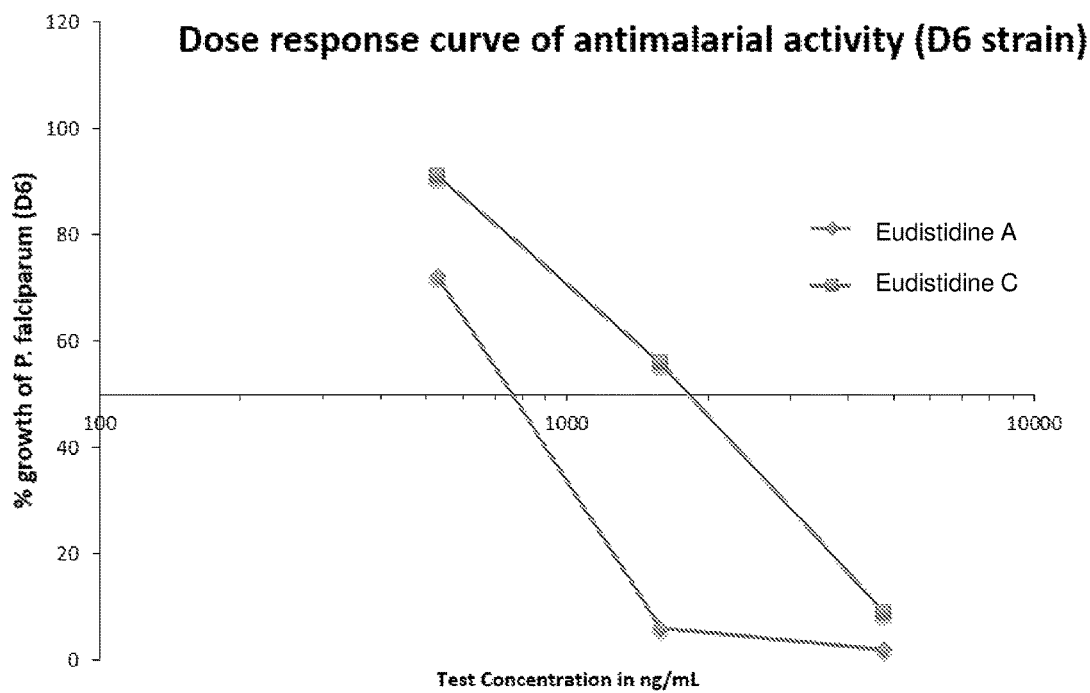
FIG. 9 is a dose response curve showing growth inhibition of *P. falciparum* D6 with eudistidine A and eudistidine C.
Figure 10:
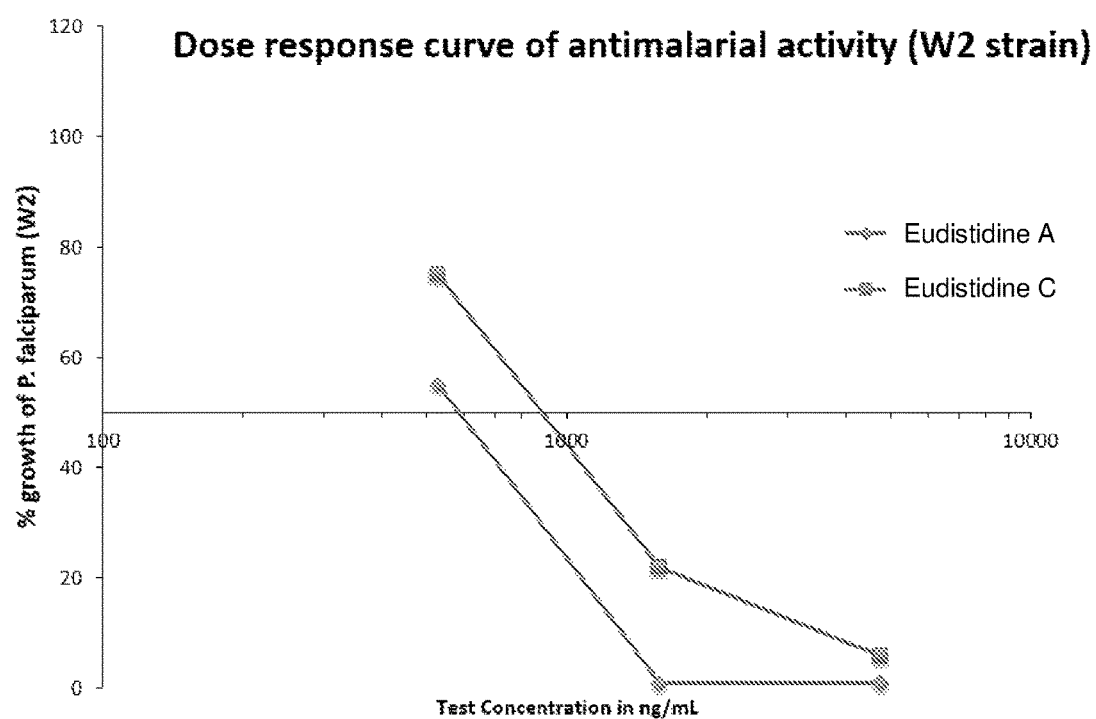
FIG. 10 is a dose response curve showing growth inhibition of *P. falciparum* W2 with eudistidine A and eudistidine C.

Both eudistidines possessed anti-malarial activity as shown in Tables 6 and 7 and in FIGS. 9 and 10. Table 6 and FIG. 9 show the dose response of eudistidine A and eudistidine C against D6. Eudistidine A had an $IC_{50}$ value of 770 ng/mL against D6 and eudistidine C had an $IC_{50}$ value of 1700 ng/mL. Table 7 and FIG. 10 show the dose response of eudistidine A and eudistidine C against W2. Surprisingly, the compounds were even more effective against the chloroquine-resistant W2 strain. Eudistidine A had an $IC_{50}$ value of 580 ng/mL against W2 and eudistidine C had an $IC_{50}$ value of 900 ng/mL. In comparison, chloroquine had an $IC_{50}$ of 15.4 ng/mL against D6 and 161 ng/mL against W2; artemisinin had an $IC_{50}$ of 7.2 ng/mL against D6 and 4.1 ng/mL against W2. None of the compounds were cytotoxic to VERO cells up to the highest tested concentration of 4760 ng/mL.

TABLE 6

Inhibition of *P. falciparam* (D6) growth by eudistidine A and eudistidine C

| | % growth of D6 strain of *P. falciparum* | | | |
|---|---|---|---|---|
| Compound | 4760 ng/mL | 1586.67 ng/mL | 528.89 ng/mL | $IC_{50}$ |
| Eudistidine A | 2 | 6 | 72 | 770 ng/mL |
| Eudistidine C | 9 | 56 | 91 | 1700 ng/mL |

TABLE 7

Inhibition of *P. falciparam* (W2) growth by eudistidine A and eudistidine C

| | % growth of W2 strain of *P. falciparum* | | | |
|---|---|---|---|---|
| Compound | 4760 ng/mL | 1586.67 ng/mL | 528.89 ng/mL | $IC_{50}$ |
| Eudistidine A | 1 | 1 | 55 | 580 ng/mL |
| Eudistidine C | 6 | 22 | 75 | 900 ng/mL |

Example 8

Treatment with the Disclosed Compounds

A subject having, or being at risk of developing, a condition characterized at least in part by HIF-1-mediated hypoxia is selected for treatment. The subject may be identified, for example, as having a solid tumor. The subject may be identified as having, or being at risk of developing, malaria. Or, the subject may be identified as having, or being at risk of developing, an inflammatory condition, such as a malignant tumor, intestinal inflammation, lung inflammation, ischemia, atherosclerosis, myocardial infarction, rheumatoid arthritis, or a healing wound. The subject may be selected based on a clinical presentation that suggests a condition that may be ameliorated by inhibiting HIF-1 activity, or by performing tests to demonstrate presence of a tumor, infection with a *Plasmodium* species, and/or one or more elevated biomarkers of inflammation.

The subject is treated by administering a compound according to Formula I or a pharmaceutically acceptable salt thereof at a dose determined by a clinician to be therapeutically effective, thereby inhibiting HIF-1 activation in the subject. The compound or salt thereof may be administered in the form of a pharmaceutical composition. The duration of treatment is a period of time sufficient to cure the condition or otherwise improve the clinical condition of the subject. Improvement or cure may be determined by clinical signs or symptoms or by diagnostic tests. For example, imaging studies are performed to determine reduction in a tumor growth rate, cessation of growth, and/or reduction in size. Diagnostic testing is used to determine absence of infection with a *Plasmodium* species, or improvement in clinical signs of malarial infection (e.g., chills, fever, sweating, headache, fatigue, nausea, vomiting, diarrhea, anemia) is noted. Diagnostic testing is used to demonstrate reduction in one or more biomarkers of inflammation, or improvement in clinical signs of inflammation (e.g., pain, redness, swelling) is noted.

A second therapeutic agent may also be administered to the subject. The second therapeutic agent may be, for example, an anticancer agent, an antimalarial agent, or an anti-inflammatory agent. The second therapeutic agent may be administered concurrently with the compound or salt thereof, or it may be administered separately before or after administration of the compound or salt thereof. The second therapeutic agent may be administered by the same route or a different route. If administered concurrently, the compound (or salt thereof) and the second therapeutic agent may be combined in a single pharmaceutical composition or may be administered concurrently as two pharmaceutical compositions.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound having a chemical structure according to Formula I or a pharmaceutically acceptable salt thereof

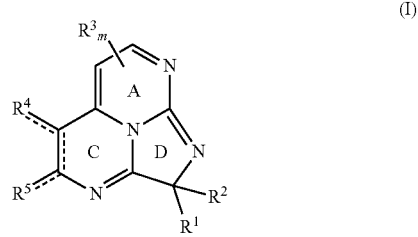

(I)

wherein each bond depicted as "------" is a single or double bond as needed to satisfy valence requirements;

$R^1$ is —$OR^a$, aryl, heteroaryl, halo, aliphatic, heteroaliphatic, alicyclic, heteroalicyclic, —$SR^a$, —$COOR^a$, or —$N(R^a)_2$, and $R^2$ is —$OR^a$, —$SR^a$, alicyclic, heteroalicyclic, aryl, or heteroaryl; or $R^1$ and $R^2$ together are =O or =S;

each $R^3$ independently is aryl, heteroaryl, aliphatic, heteroaliphatic, —$COOR^a$, or —$C(O)N(R^a)_2$;

m is 0, 1, or 2;

$R^4$ and $R^5$ together with the carbon atoms to which they are bound define a ring B where the ring B is aryl, heteroaryl, alicyclic, or heteroalicyclic, or $R^4$ and $R^5$ independently are hydrogen, aliphatic, heteroaliphatic, halo, —$OR^a$, —$SR^a$, oxygen, or sulfur; and each $R^a$ independently is hydrogen or alkyl, wherein the compound is not a naturally occurring compound.

2. The compound of claim 1, wherein the compound has a chemical structure according to Formula II:

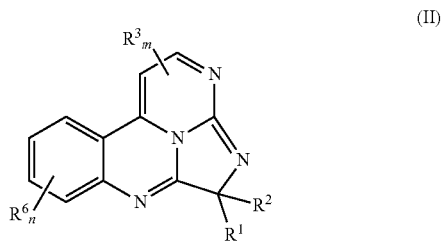

(II)

wherein:

n is 0, 1, 2, 3, or 4; and each $R^6$ independently is aliphatic, heteroaliphatic, alicyclic, heteroalicyclic, aryl, heteroaryl, halo, —$OR^a$, —$SR^a$, —$COOR^a$, or —$C(O)N(R^a)_2$, where each $R^a$ independently is hydrogen or alkyl.

3. The compound of claim 1, wherein m is 0.

4. The compound of claim 2, wherein n is 0.

5. The compound of claim 1, wherein:

(i) $R^1$ is hydroxyl, lower alkoxy, lower aliphatic, alicyclic, or aryl; or (ii) $R^2$ is aryl or heteroaryl; or (iii) both (i) and (ii).

6. The compound of claim 1, wherein:
R[1] is:
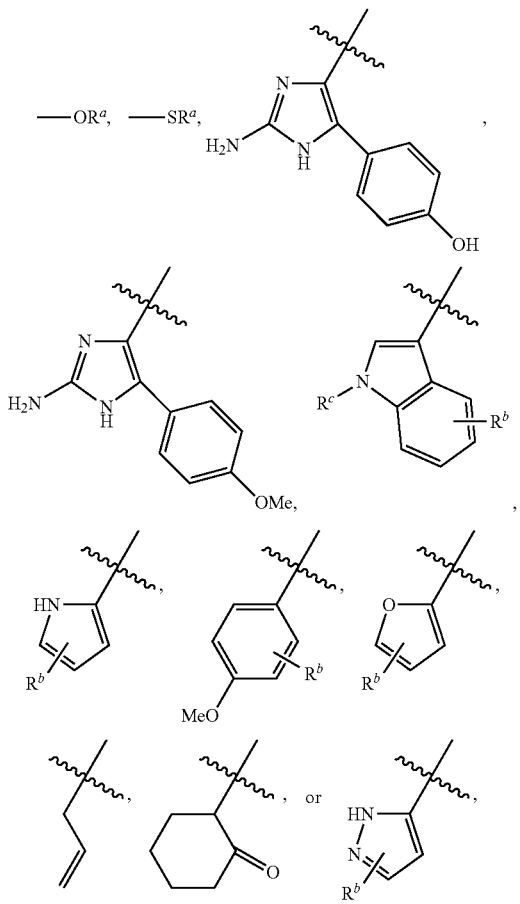
wherein R[b] is hydrogen, halo, aliphatic, heteroaliphatic, —OR[a], —SR[a], —C(O)OR[a], or —C(O)N(R[a])$_2$; and
R[c] is hydrogen, aliphatic, or heteroaliphatic;
optionally wherein R[2] is:
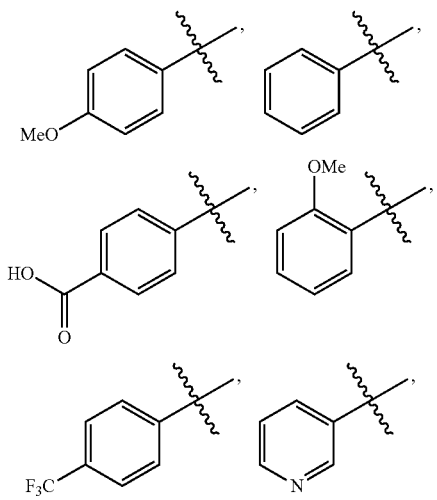
7. The compound of claim 1, wherein the compound is:
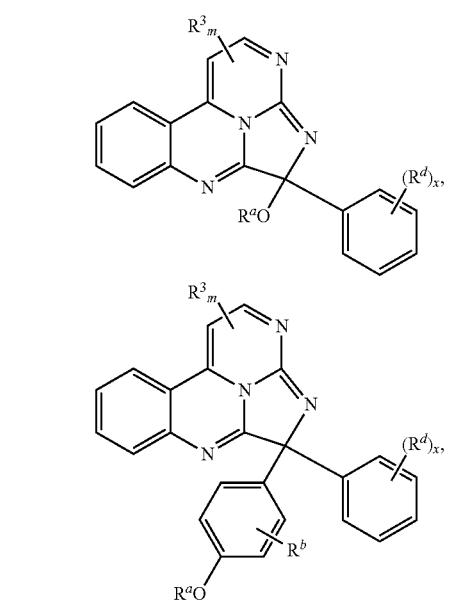

-continued
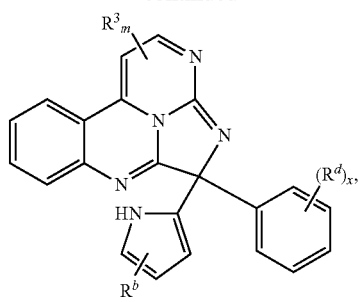
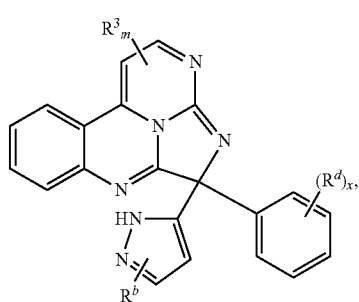
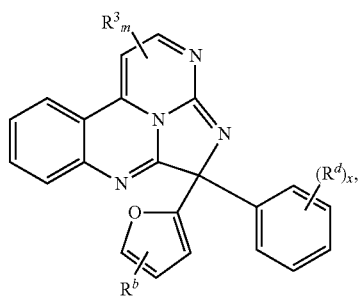
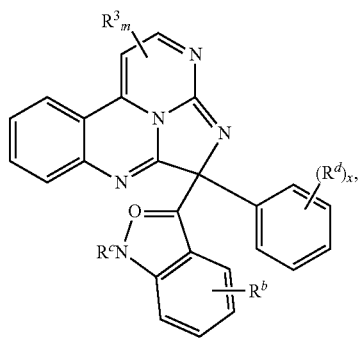
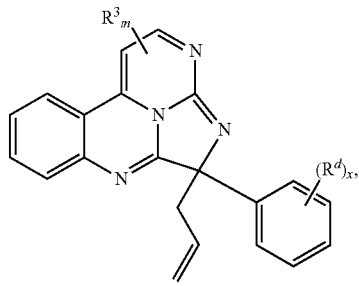
-continued
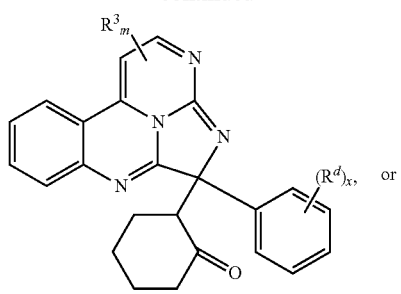
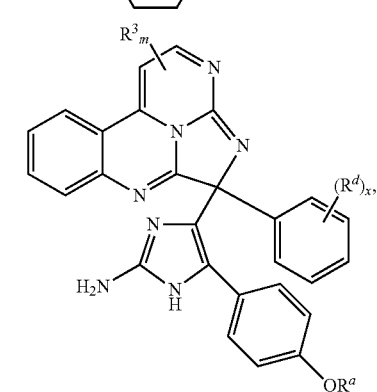
wherein $R^b$ is hydrogen, halo, aliphatic, heteroaliphatic, —$OR^a$, —$SR^a$, —$C(O)OR^a$, or —$C(O)N(R^a)_2$;
$R^c$ is hydrogen, aliphatic, or heteroaliphatic;
each $R^d$ independently is —$OR^a$, hydrogen, halo, aliphatic, heteroaliphatic, amido, —$SR^a$, or aryl; and
x is 0, 1, 2, or 3.
8. The compound of claim 1, wherein the compound is:
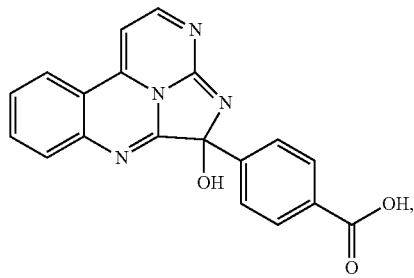
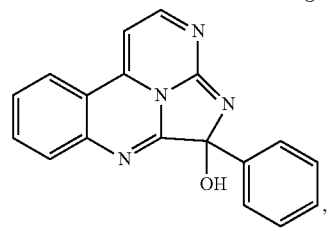
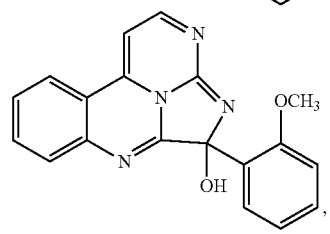

63
-continued
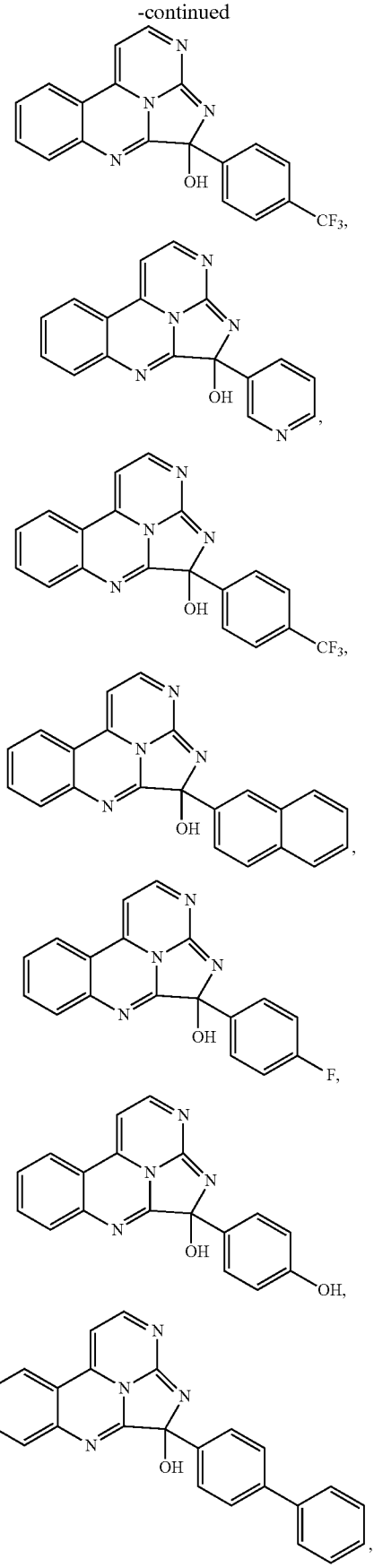
64
-continued
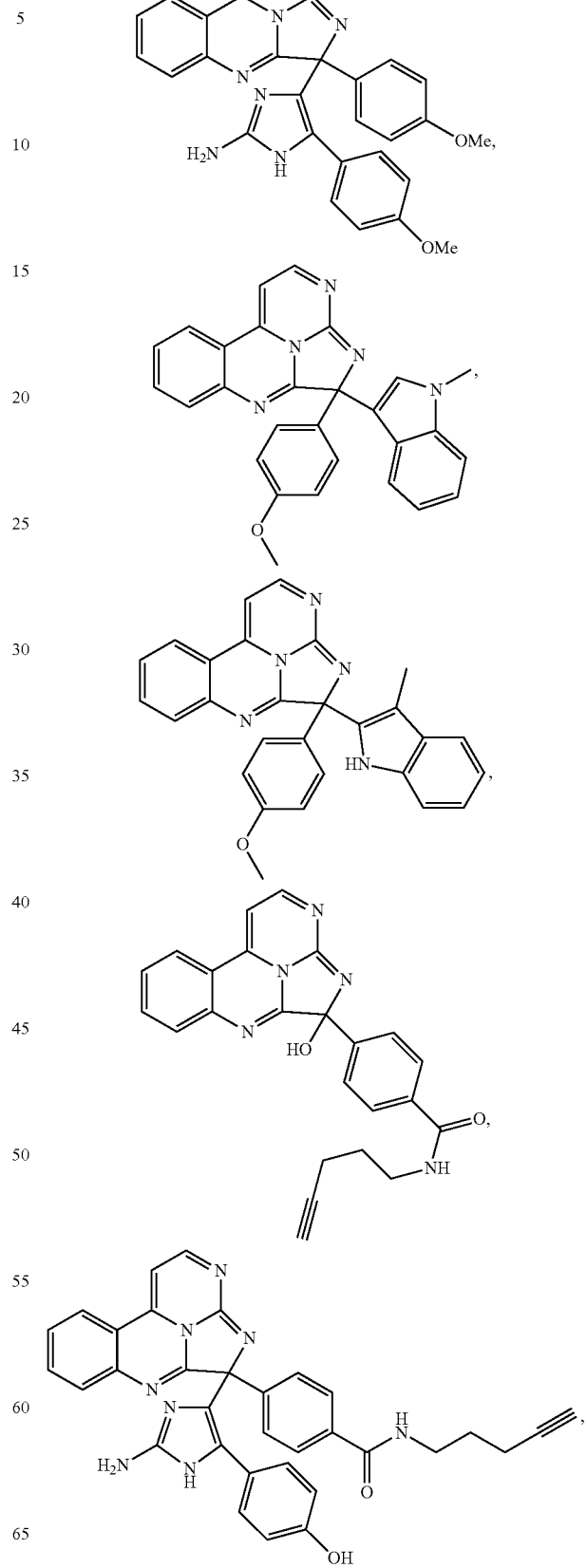

-continued

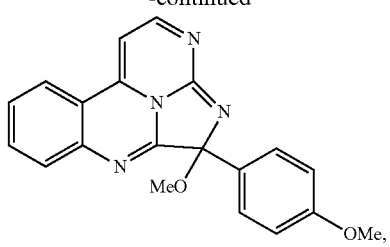

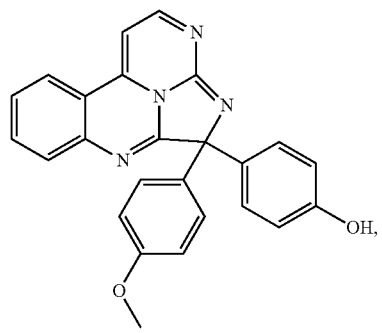

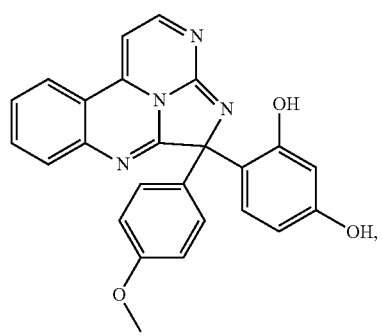

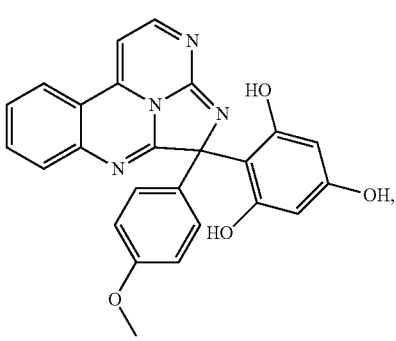

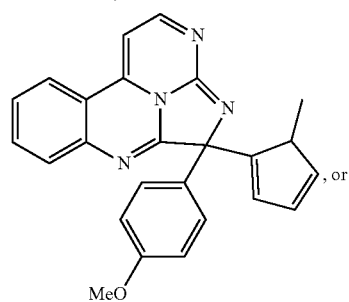

-continued

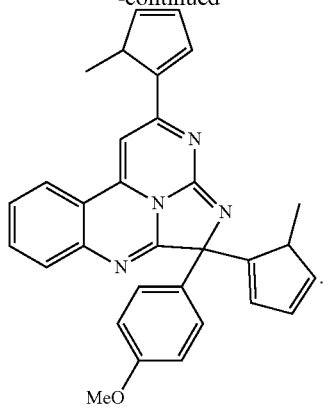

9. A pharmaceutical composition comprising:
   (i) at least one compound or pharmaceutically acceptable salt thereof, the compound having a chemical structure according to Formula I or a pharmaceutically acceptable salt thereof

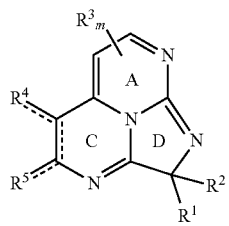

(I)

wherein each bond depicted as "------" is a single or double bond as needed to satisfy valence requirements, $R^1$ is —$OR^a$, aryl, heteroaryl, halo, aliphatic, heteroaliphatic, alicyclic, heteroalicyclic, —$SR^a$, —$COOR^a$, or —$N(R^a)_2$, and $R^2$ is —$OR^a$, —$SR^a$, alicyclic, heteroalicyclic, aryl, or heteroaryl; or $R^1$ and $R^2$ together are =O or =S, each $R^3$ independently is aryl, heteroaryl, aliphatic, heteroaliphatic, —$COOR^a$, or —$C(O)N(R^a)_2$, m is 0, 1, or 2, $R^4$ and $R^5$ together with the carbon atoms to which they are bound define a ring B where the ring B is aryl, heteroaryl, alicyclic, or heteroalicyclic, or $R^4$ and $R^5$ independently are hydrogen, aliphatic, heteroaliphatic, halo, —$OR^a$, —$SR^a$, oxygen, or sulfur, and each $R^a$ independently is hydrogen or alkyl; and (ii) at least one pharmaceutically acceptable carrier.

10. The pharmaceutical composition of claim 9, further comprising a second therapeutic agent.

11. A method of making a compound according to claim 1, comprising:
    (i) heating compound A, wherein R' is hydrogen or $R^3$, with 1,1-dimethoxy-N,N'-dimethylmethanamine to form an intermediate

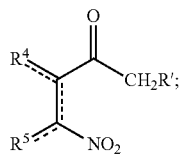
(A)

(ii) refluxing a solution comprising the intermediate and guanidine hydrochloride to form compound B

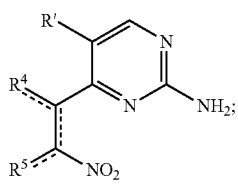
(B)

(iii) hydrogenating compound B with a catalyst comprising Pd/C to form compound C

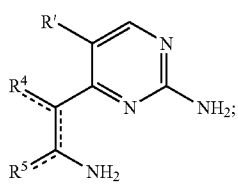
(C)

(iv) oxidizing $R^2$—C(O)CH$_2$X to form $R^2$—C(O)C(O)H, where X is halo;

(v) if $R^2$ is —OH or —SH, heating compound C with the $R^2$—C(O)C(O)H to form compound D where A is O or S; or if $R^2$ is other than —OH or —SH, heating compound C with the $R^2$—C(O)C(O)H, followed by addition of an oxidant to form compound E

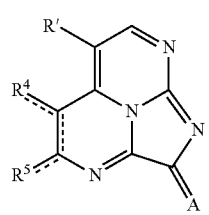
(D)

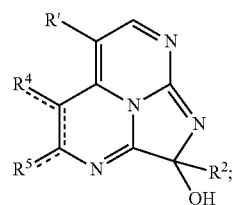
(E)

and (vi) optionally reacting compound E with a nucleophile comprising $R^1$ to form compound F

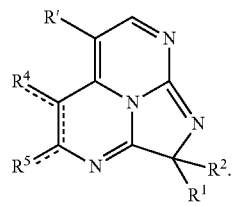
(F)

12. The method of claim 11, wherein:
$R^4$ and $R^5$ together with the carbon atoms to which they are bound define an optionally substituted phenyl ring; or
R' is hydrogen; or
$R^1$ is hydroxyl, lower alkoxy, lower aliphatic, alicyclic, or aryl; or
$R^2$ is aryl or heteroaryl; or
any combination thereof.

13. The method of claim 11, wherein the nucleophile comprising $R^1$ is $R^1$H.

14. A method for inhibiting hypoxia-inducible factor 1 (HIF-1) activity, comprising contacting a cell with an effective amount of a compound or pharmaceutically acceptable salt thereof, the compound having a chemical structure according to Formula I

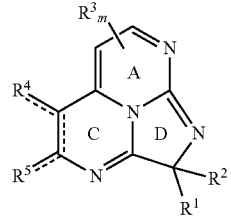
(I)

wherein each bond depicted as "------" is a single or double bond as needed to satisfy valence requirements,
$R^1$ is —OR$^a$, aryl, heteroaryl, halo, aliphatic, heteroaliphatic, alicyclic, heteroalicyclic, —SR$^a$, —COOR$^a$, or —N(R$^a$)$_2$, and $R^2$ is —OR$^a$, —SR$^a$, alicyclic, heteroalicyclic, aryl, or heteroaryl; or $R^1$ and $R^2$ together are =O or =S,
each $R^3$ independently is aryl, heteroaryl, aliphatic, heteroaliphatic, —COOR$^a$, or —C(O)N(R$^a$)$_2$,
m is 0, 1, or 2,
$R^4$ and $R^5$ together with the carbon atoms to which they are bound define a ring B where the ring B is aryl, heteroaryl, alicyclic, or heteroalicyclic, or $R^4$ and $R^5$ independently are hydrogen, aliphatic, heteroaliphatic, halo, —OR$^a$, —SR$^a$, oxygen, or sulfur, and
each $R^a$ independently is hydrogen or alkyl.

15. The method of claim 14, further comprising contacting the cell with a second therapeutic agent.

16. The method of claim 15, wherein the second therapeutic agent is an anticancer agent, an antimalarial agent, or an anti-inflammatory agent.

17. A method, comprising administering to a subject a therapeutically effective amount of:
(i) a compound, or a pharmaceutically acceptable salt thereof, the compound having a chemical structure according to Formula I

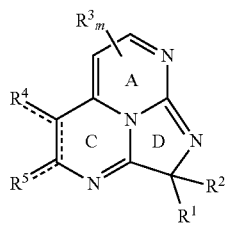

(I)

wherein each bond depicted as "------" is a single or double bond as needed to satisfy valence requirements, $R^1$ is —$OR^a$, aryl, heteroaryl, halo, aliphatic, heteroaliphatic, alicyclic, heteroalicyclic, —$SR^a$, —$COOR^a$, or —$N(R^a)_2$, and $R^2$ is —$OR^a$, —$SR^a$, alicyclic, heteroalicyclic, aryl, or heteroaryl; or $R^1$ and $R^2$ together are =O or =S, each $R^3$ independently is aryl, heteroaryl, aliphatic, heteroaliphatic, —$COOR^a$, or —$C(O)N(R^a)_2$, m is 0, 1, or 2, $R^4$ and $R^5$ together with the carbon atoms to which they are bound define a ring B where the ring B is aryl, heteroaryl, alicyclic, or heteroalicyclic, or $R^4$ and $R^5$ independently are hydrogen, aliphatic, heteroaliphatic, halo, —$OR^a$, —$SR^a$, oxygen, or sulfur, and each $R^a$ independently is hydrogen or alkyl, or (ii) a pharmaceutical composition comprising the compound or pharmaceutically acceptable salt thereof and at least one pharmaceutically acceptable carrier.

18. The method of claim 17, wherein the subject has a solid tumor, malaria, or an inflammatory condition mediated by HIF-1.

19. The method of claim 18, wherein administering comprises:

administering to the subject a pharmaceutical composition comprising (i) the compound or pharmaceutically acceptable salt thereof, (ii) a second therapeutic agent, and (iii) at least one pharmaceutically acceptable carrier; or separately administering in any order to the subject (i) the compound or pharmaceutically acceptable salt thereof and (ii) a second therapeutic agent.

20. The method of claim 18, wherein the inflammatory condition is a malignant tumor, intestinal inflammation, lung inflammation, ischemia, atherosclerosis, myocardial infarction, rheumatoid arthritis, or a healing wound.

21. The method of claim 11, wherein:

heating compound C with the $R^2$—C(O)C(O)H to form compound D comprises heating at 50-70° C. for several hours; and heating compound C with the $R^2$—C(O)C(O)H, followed by addition of an oxidant to form compound E comprises heating compound C with the $R^2$—C(O)C(O)H for 50-70° C. for 15-60 minutes.

22. The compound of claim 1, wherein the compound is not eudistidine A, eudistidine B, or eudistidine C:

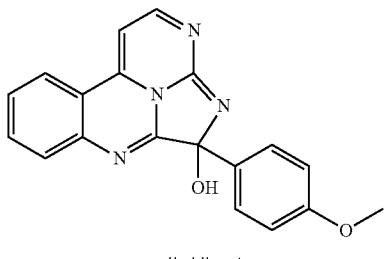

eudistidine A

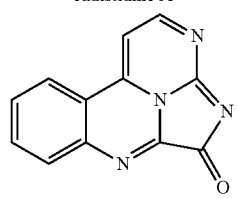

eudistidine B

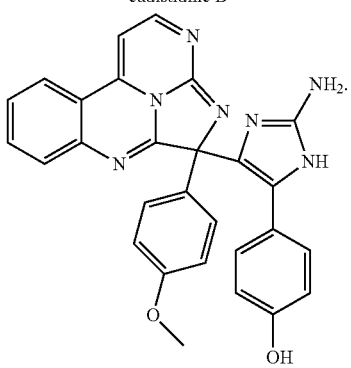

eudistidine C

* * * * *